United States Patent
Ohno et al.

(10) Patent No.: US 7,595,093 B2
(45) Date of Patent: Sep. 29, 2009

(54) CONDENSED POLYCYCLIC AROMATIC COMPOUND THIN FILM AND METHOD FOR PREPARING CONDENSED POLYCYCLIC AROMATIC COMPOUND THIN FILM

(75) Inventors: Eiichi Ohno, Fuji (JP); Yutaka Natsume, Fuji (JP); Takashi Minakata, Shizuoka (JP)

(73) Assignee: Asahi Kasei Corporation, Osaka (JP)

( * ) Notice: Subject to any disclaimer, the term of this patent is extended or adjusted under 35 U.S.C. 154(b) by 364 days.

(21) Appl. No.: 10/592,093

(22) PCT Filed: Mar. 9, 2005

(86) PCT No.: PCT/JP2005/004125

§ 371 (c)(1),
(2), (4) Date: Sep. 7, 2006

(87) PCT Pub. No.: WO2005/087390

PCT Pub. Date: Sep. 22, 2005

(65) Prior Publication Data

US 2007/0184574 A1   Aug. 9, 2007

(30) Foreign Application Priority Data

Mar. 10, 2004 (JP) ............................ 2004-066674
Mar. 24, 2004 (JP) ............................ 2004-087060
Mar. 29, 2004 (JP) ............................ 2004-096420
Jun. 25, 2004 (JP) ............................ 2004-188605

(51) Int. Cl.
   *B05D 3/00* (2006.01)
(52) U.S. Cl. .................................. 427/384; 427/385.5
(58) Field of Classification Search ....................... None
See application file for complete search history.

(56) References Cited

U.S. PATENT DOCUMENTS 3,403,165 A * 9/1968 Matsunaga .................. 549/31

(Continued)

FOREIGN PATENT DOCUMENTS

EP   1 416 069 A1   5/2004

(Continued)

OTHER PUBLICATIONS

Christos D. Dimitrakopoulos et al., Adv. Mater. vol. 14, No. 2, pp. 99-117 Jan. 16, 2002.

(Continued)

*Primary Examiner*—Erma Cameron
(74) *Attorney, Agent, or Firm*—Birch, Stewart, Kolasch & Birch, LLP

(57) ABSTRACT

An organic semiconductor thin film exhibiting high mobility and a method for preparing the same, and a material for preparing the organic semiconductor thin film by a wet process and a method for preparing the same are provided. Further, an organic semiconductor device excellent in electronic characteristics is provided. A mixture of high purity pentacene and 1,2,4-trichlorobenzene was heated to prepare a homogeneous solution, and a silicon substrate having a pattern of a gold electrode as a source/drain electrode formed thereon was heated to 100° C. and the resultant pentacene solution was spread on the surface of the substrate. When 1,2,4-trichlorobenzene was evaporated, a pentacene thin film was formed. A transistor was formed with the use of the thin film.

20 Claims, 8 Drawing Sheets

U.S. PATENT DOCUMENTS 5,936,259 A 8/1999 Katz et al.
7,061,010 B2 * 6/2006 Minakata .................. 257/40

FOREIGN PATENT DOCUMENTS

| | | |
|---|---|---|
| JP | 11-195790 A | 7/1999 |
| JP | 2000-307172 A | 11/2000 |
| JP | 2003-347624 A | 12/2003 |
| JP | 2004-43408 A | 2/2004 |
| JP | 2004-47566 A | 2/2004 |
| JP | 2004-269431 A | 9/2004 |
| JP | 2005-91231 A | 4/2005 |
| WO | WO-03/016599 A1 | 2/2003 |

OTHER PUBLICATIONS

C.D. Dimitrakopoulos et al., J. Appl. Phys. 80(4), pp. 2501-2508 Aug. 15, 1996.
Hagen Klauk et al., IEEE Transactions on Electron Devices, vol. 46, No. 6, pp. 1258-1263, Jun. 1999.
A.R. Brown et al., J. Appl. Phys. 79(4), pp. 2136-2138, Feb. 15, 1996.
Tamotsu Takahashi et al., J. Am. Chem. Soc. vol. 122, pp. 12876-12877, 2000.
Ron J. Graham et al., J. Org. Chem., vol. 60, pp. 5770-5777, 1995.
Glen P. Miller et al., Organic Letters, vol. 2, No. 25, pp. 3979-3982, 2000.
Hong Meng et al., Adv. Mater., vol. 15, No. 13, pp. 1090-1093, Jul. 4, 2003.
Dmitrii F. Perepichka et al., J. Am. Chem. Soc., vol. 125, pp. 10190-10191, 2003.

* cited by examiner

US 7,595,093 B2

CONDENSED POLYCYCLIC AROMATIC COMPOUND THIN FILM AND METHOD FOR PREPARING CONDENSED POLYCYCLIC AROMATIC COMPOUND THIN FILM

TECHNICAL FIELD

The present invention relates to an organic semiconductor thin film, a method for preparing the same, and an organic semiconductor device. The present invention also relates to a high-purity condensed polycyclic aromatic compound and a method for refining a condensed polycyclic aromatic compound. The present invention further relates to a method for determining the amount of impurities contained in a condensed polycyclic aromatic compound.

BACKGROUND ART

A device with the use of an organic semiconductor is prepared with a milder film-forming condition than a conventional inorganic semiconductor device, so that the semiconductor thin film can be formed on various substrates and can be formed at ordinary temperature. For this reason, it is expected to reduce the preparation cost and to make the device flexible by forming the thin film on a polymer film or the like.

As for an organic semiconductor material, an aromatic compound has been studied which includes predominantly: a polyacene compound such as anthracene, tetracene and pentacene as well as a conjugate macromolecular compound such as polyphenylenevinylene, polypyrrole and polythiophene, and an oligomer thereof. It has been reported that the polyacene compound particularly has high crystallinity because of having a high intermolecular cohesive force, and thereby exhibits high carrier mobility and excellent characteristics as a semiconductor device.

The form of a polyacene compound to be used in a device has been a vapor deposition film or a single crystal. The device has been investigated to be applied to a transistor, a solar cell, a laser and the like (see Non-Patent Documents 1 to 3).

As for a method to form a thin film of a polyacene compound with a method other than a vacuum deposition method, a method has been reported which applies a solution of a precursor of pentacene, which is one of polyacene compounds, onto a substrate and heats the wet film to form a pentacene thin film (see Non-Patent Document 4). A condensed polycyclic aromatic compound like the polyacene compound has low solubility to a general solvent, is hardly formed into a thin film from its solution by a wet process. Accordingly, the method forms the thin film with the use of the solution of the precursor having high solubility and converts the precursor to the polyacene compound by heat.

On one hand, a polyacene compound having a substituent is described in a report (Non-Patent Document 5) by Takahashi et al., a report (Non-Patent Document 6) by Graham et al., and a report (Non-Patent Document 7) by Mirror et al. Furthermore, Non-Patent Document 8 describes an example of synthesis for 2,3,9,10-tetramethylpentacene, and Non-Patent Document 9 describes an example of synthesis for 2,3,9,10-tetrachloropentacene.

However, examples are not reported in which a thin film of a polyacene compound such as pentacene is formed from a solution of the polyacene compound, and in which a semiconductor device is composed with the use of the thin film. An example of forming the thin film from the solution of an oligothiophene derivative is reported in Patent Document 1.

On the other hand, the performance of an organic semiconductor device provided with a condensed polycyclic aromatic compound thin film has relevance to the purity of the condensed polycyclic aromatic compound, and it is important to increase the purity of the condensed polycyclic aromatic compound (decrease contents of impurities), in order to enhance the performance such as mobility. It has not been easy to obtain an organic semiconductor material of high purity such as a condensed polycyclic aromatic compound, but Patent Document 2 proposes a method of purifying the material with the use of a supercritical fluid.

However, a method of forming the thin film of a polyacene compound with the use of the precursor as described above had a problem that high-temperature treatment is necessary for converting the above described precursor to the polyacene compound (for instance, about 150 to 200° C. for pentacene). In addition, the method concurrently had a problem that an unreacted part remains as a defect because it is difficult to completely convert the precursor into the polyacene compound, and that denaturation occurs due to a high temperature and forms the defect.

In addition, a purifying method according to Patent Document 2 can increase the purity of an organic semiconductor material such as a condensed polycyclic aromatic compound, but a purifying method for further increasing the purity has been demanded in recent years because an organic semiconductor device having higher performance has been required.

For this reason, an object of the present invention is to solve the above described problems of the conventional technology, and to provide an organic semiconductor thin film exhibiting high mobility and a preparing method therefor. Another object of the present invention is concomitantly to provide an organic semiconductor device having excellent electronic characteristics. Still another object of the present invention is concurrently to provide a high-purity condensed polycyclic aromatic compound; a method for purifying a condensed polycyclic aromatic compound; and a method for determining the amount of impurities in the condensed polycyclic aromatic compound.

Patent Document 1: JP2000-307172A
Patent Document 2: JP2003-347624A
Non-Patent Document 1: "Advanced Materials", Vol. 14, p. 99, 2002
Non-Patent Document 2: Dimitrakopoulos et al., "Journal of Applied Physics", Vol. 80, p. 2501, 1996
Non-Patent Document 3: Croke et al., "IEEE Transaction on Electron Devices", Vol. 46, p. 1258, 1999
Non-Patent Document 4: Brown et al., "Journal of Applied Physics", Vol. 79, p. 2136, 1996
Non-Patent Document 5: Takahashi et al., "Journal of American Chemical Society", Vol. 122, p. 12876, 2000
Non-Patent Document 6: Graham et al., "Journal of Organic Chemistry", Vol. 60, p. 5770, 1995
Non-Patent Document 7: Mirror et al., "Organic Letters", Vol. 2, p. 3979, 2000
Non-Patent Document 8: "Advanced Materials", Vol. 15, p. 1090, 2003
Non-Patent Document 9: "Journal of American Chemical Society", Vol. 125, p. 10190, 2003

DISCLOSURE OF THE INVENTION

In order to solve the above described problems, the present invention has the following constitution. Specifically, the method for preparing a condensed polycyclic aromatic compound thin film according to the present invention is characterized in that the method comprises the steps of: dissolving a condensed polycyclic aromatic compound in a solvent containing an organic compound having a higher vapor pressure than that of the condensed polycyclic aromatic compound at a higher temperature than ordinary temperature to form the solution; spreading the solution having a higher temperature than ordinary temperature over a base having a higher temperature than ordinary temperature; and removing the organic compound and the solvent from the solution spread over the base to form a condensed polycyclic aromatic compound thin film having the condenced polycyclic aromatic compound.

The condensed polycyclic aromatic compound can be at least one of a polyacene compound and a derivative thereof. The condensed polycyclic aromatic compound further can be at least one of pentacene, a derivative of pentacene, hexacene and a derivative of hexacene.

In the method for preparing a condensed polycyclic aromatic compound thin film according to the present invention, a temperature of the solution when the condensed polycyclic aromatic compound is dissolved in the solvent and the temperature of the solution when it is spread over the base are preferably higher than 60° C. but 250° C. or lower, more preferably are higher than 70° C. but 240° C. or lower, further preferably are higher than 80° C. but 230° C. or lower, and most preferably are higher than 100° C. but 220° C. or lower.

In addition, in the method for preparing a condensed polycyclic aromatic compound thin film according to the present invention, the temperature of the base is preferably 60° C. or higher but 230° C. or lower, more preferably is higher than 70° C. but 220° C. or lower, and further preferably is higher than 80° C. but 210° C. or lower.

In the method for preparing a condensed polycyclic aromatic compound thin film according to the present invention, the temperature of the solution when spread over the base is also preferably equal to or higher than the temperature of the base. Furthermore, a value obtained by subtracting the temperature of the base from the temperature of the solution is preferably −15° C. or higher but 190° C. or lower, more preferably is 0° C. or higher but 100° C. or lower, and further preferably is 0° C. or higher but 80° C. or lower.

In addition, in the method for preparing a condensed polycyclic aromatic compound thin film according to the present invention, it is preferable to carry out the respective steps in an inert gas atmosphere.

The method for purifying a condensed polycyclic aromatic compound according to the present invention is a method for reducing the amount of impurities contained in the condensed polycyclic aromatic compound, the method comprising the steps of: dissolving a condensed polycyclic aromatic compound in a solvent containing an organic compound having a higher vapor pressure than that of the condensed polycyclic aromatic compound at a higher temperature than ordinary temperature to form a solution; and cooling the solution or mixing the solution with a solvent in which the condensed polycyclic aromatic compound is poorly soluble to precipitate a crystal of the condensed polycyclic aromatic compound from the solution. In the above description, the impurities can be a quinone compound.

The condensed polycyclic aromatic compound according to the present invention is a high-purity condensed polycyclic aromatic compound obtained by the method for purifying a condensed polycyclic aromatic compound according to the present invention, and includes 1 mass % or less of a quinone compound.

The method for determining the amount of impurities according to the present invention is a method for determining the amount of the impurities contained in a condensed polycyclic aromatic compound, and comprises the steps of: dissolving a condensed polycyclic aromatic compound into a solvent containing an organic compound having a higher vapor pressure than that of the condensed polycyclic aromatic compound at a higher temperature than ordinary temperature to form a solution; and measuring the spectrum of the solution.

The condensed polycyclic aromatic compound thin film according to the present invention is obtained by the method for preparing a condensed polycyclic aromatic compound thin film according to the present invention.

The condensed polycyclic aromatic compound thin film according to the present invention is a condensed polycyclic aromatic compound thin film having crystallinity, wherein a molecule of a condensed polycyclic aromatic compound is oriented so that the major axis of the molecule is perpendicular to the surface of the thin film, and the thin film shows a wide angle X-ray diffraction pattern having a half peak width of a diffraction peak for a (001) plane among the diffraction peaks for (00n) planes in 0.05 deg or more but 0.2 deg or less.

The condensed polycyclic aromatic compound thin film preferably has at least one of a structure consisting of plate crystals with particle sizes of 3 μm or larger and a structure having the plate crystals extended into a sheet shape.

Furthermore, the pentacene thin film according to the present invention shows a wide angle X-ray diffraction pattern having diffraction peaks for (00n) planes (n is an integer of 1 or more) corresponding to an interplanar distance of 1.4 nm or more but less than 1.5 nm, in which a ratio (I)/(I') of the intensity (I) of a diffraction peak for a (001) plane among the diffraction peaks to the intensity (I') of a diffraction peak for a (001) plane corresponding to an interplanar distance of 1.5 nm or more but less than 1.6 nm exceeds 10, and a half peak width of the diffraction peak for a (001) plane among the diffraction peaks for (00n) planes (n is an integer of 1 or more) corresponding to an interplanar distance of 1.4 nm or more but less than 1.5 nm is 0.08 deg or more but 0.2 deg or less.

The organic semiconductor device according to the present invention is at least partially constituted by the condensed polycyclic aromatic compound thin film or the pentacene thin film according to the present invention.

According to the method for preparing a condensed polycyclic aromatic compound thin film according to the present invention, a condensed polycyclic aromatic compound thin film poorly soluble in a common solvent can be formed by a wet process. In addition, the condensed polycyclic aromatic compound thin film according to the present invention has high mobility. Furthermore, the organic semiconductor device according to the present invention has excellent electron characteristics.

Furthermore, the method for purifying a condensed polycyclic aromatic compound according to the present invention can prepare a high-purity condensed polycyclic aromatic compound. In addition, the condensed polycyclic aromatic compound according to the present invention contains few impurities and is highly pure, and accordingly can impart high performance to an organic semiconductor thin film or an organic semiconductor device, when used for preparing it. The method for determining the amount of impurities according to the present invention can determine the content of the impurities contained in the condensed polycyclic aromatic compound, and accordingly can contribute to the quality control and performance stabilization of the organic semiconductor thin film or the organic semiconductor device, by preparing the organic semiconductor thin film or the organic semiconductor device with the use of the condensed polycyclic aromatic compound of which the content of the impurities has been quantified.

BEST MODE FOR CARRYING OUT THE INVENTION

Figure 1:
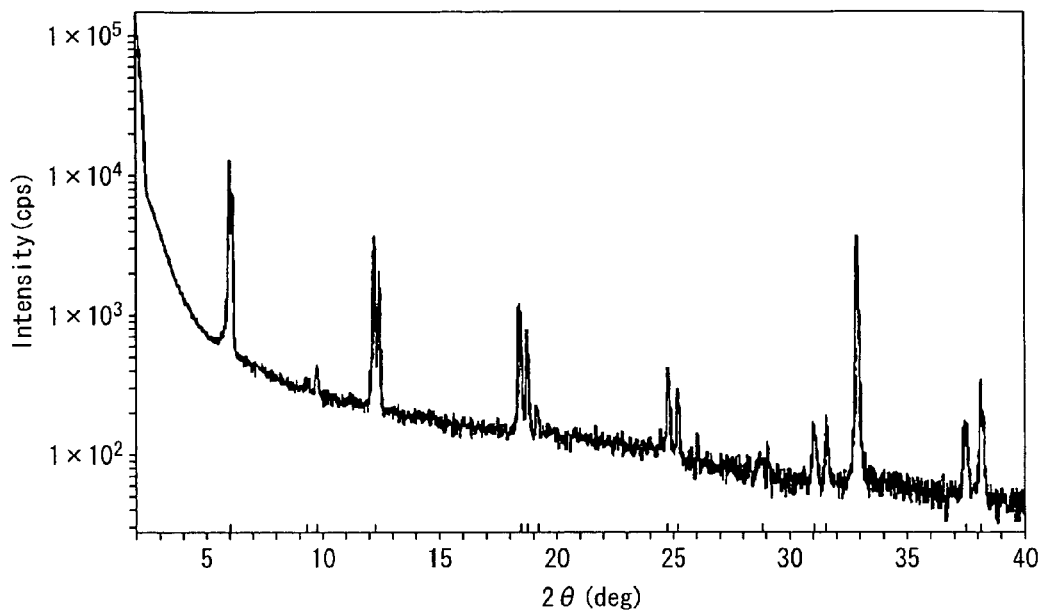
FIG. 1 is a view showing a wide angle X-ray diffraction pattern of a pentacene thin film in Example 1.

The condensed polycyclic aromatic compound thin film according to the present invention is prepared by a wet process from a solution obtained by dissolving a condensed polycyclic aromatic compound in a solvent containing an organic compound having a higher vapor pressure than that of the condensed polycyclic aromatic compound at a higher temperature than ordinary temperature. Here, a type of the above described solvent is not limited in particular, as long as the solvent can dissolve the condensed polycyclic aromatic compound therein at a higher temperature than the ordinary temperature. For instance, a mixture of the above described organic compound and a different type of a compound from it may be used as a solvent or the organic solvent may be used alone as a solvent.

The above described solution is a homogeneous solution having a condensed polycyclic aromatic compound dissolved in a solvent, but a liquid dispersion having the compound not completely dissolved in a solvent can occasionally provide the condensed polycyclic aromatic compound thin film with a similar method. For this reason, hereafter, there may be a case where the above described solution and the liquid dispersion are described with the use of the word of a mixture which means both of the solution and the liquid dispersion.

In the first place, a condensed polycyclic aromatic compound will be described. The condensed polycyclic aromatic compound used in the present invention preferably has a polycyclic structure consisting of 2 or more but 15 or less benzene rings which have been condensed. Such a compound includes, for instance, anthracene, tetracene, pentacene, hexacene, ovalene, coronene, dibenzocoronene, hexabenzocoronene, terylene, quoterylene, isoviolanthrene, bisantene, antanthrene, circumanthracene, tetrabenzocoronene, dicoronylene, circobiphenyl, terphenylene, quaterphenylene, pentaphenylene and sexiphenylene.

Another preferable aromatic compound has a heterocycle in which a chalcogen element such as sulfur (S), selenium (Se) and tellurium (Te) substitutes for one part of carbon atoms composing an aromatic ring. Such a compound includes, for instance, tetrathiafulvalene, tetraselenafulvalene, bisethylenedithiotetrathiafulvalene and oligothiophene (such as terthiophene, quaterthiophene, pentathiophene and sexithiophene).

These condensed polycyclic aromatic compounds may be derivatives having a molecular structure in which a functional group substitutes for some or all of hydrogen atoms coupled with a benzene ring. The functional group includes, for instance, an aliphatic hydrocarbon group such as an alkyl group, an alkenyl group and an alkynyl group, an aromatic hydrocarbon group, an alkoxyl group, an ether group, a halogen group, a formyl group, an acyl group, an ester group, a mercapto group, a thioalkyl group, a sulfide group, a disulphide group, a sulphonyl group and an amide group.

Among these condensed polycyclic aromatic compounds, a polyacene compound such as tetracene, pentacene and hexacene and a derivative of the polyacene compound are preferable because of exhibiting high mobility. The reason is considered to be because a polyacene compound tends to form a herringbone structure in which the molecules are stacked on each other and the electroconductive planes form a two-dimensional network, and accordingly makes π electron orbits greatly overlapped and carriers easily move among the molecules. Furthermore, in consideration of the stability of mobility, pentacene and a pentacene derivative are further preferable.

A usable condensed polycyclic aromatic compound such as pentacene has a form of a powder, a flake and a needle crystal. In order to obtain an organic semiconductor thin film of high quality, it is preferable to use the high-purity condensed polycyclic aromatic compound. A method for purifying a condensed polycyclic aromatic compound such as pentacene includes, for instance, a sublimation purifying method and a recrystallization method which are general purifying methods. The recrystallization method is a method of obtaining the high-purity condensed polycyclic aromatic compound, by dissolving the condensed polycyclic aromatic compound in an organic compound (corresponding to solvent) capable of dissolving the condensed polycyclic aromatic compound in itself, and recrystallizing the condensed polycyclic aromatic compound from the solution.

In the next place, an example of having purified pentacene by a recrystallization method will be shown. Pentacene was dissolved in heated dichlorobenzene, and the obtained solution was cooled to make crystals of pentacene precipitated. Then, the precipitated crystal was separated with a method such as a filtration method and a centrifugal separation method, and pentacene of high purity was obtained. In such a purifying method, pentacenequinone (quinone compound) and dihydropentacene which are impurities of pentacene remain in the solution because of having high solubility to an organic compound which is a solvent. Accordingly, these impurities are hardly taken in the precipitated crystal, and the precipitated pentacene acquires enhanced purity. Particularly, dihydropentacene is hardly removed from pentacene with a sublimation purifying method, so that pentacene is preferably refined with the recrystallization method.

A condensed polycyclic aromatic compound can be also refined by dissolving a condensed polycyclic aromatic compound in an organic compound (corresponding to solvent) capable of dissolving the condensed polycyclic aromatic compound in itself to form a condensed polycyclic aromatic compound solution, and mixing a hardly soluble solvent for the condensed polycyclic aromatic compound to precipitate crystals of the condensed polycyclic aromatic compound from the condensed polycyclic aromatic compound solution. The purifying method is a method of removing impurities by using a difference of solubility to the solvent between the condensed polycyclic aromatic compound and the impurity.

In the next place, an example will be shown in which pentacene has been highly purified with the use of the difference of solubility as described above. Pentacene was dissolved in a heated solvent such as dichlorobenzene and trichlorobenzene, and a hardly soluble solvent such as ethanol and acetone was added to the obtained solution to precipitate crystals of pentacene. The precipitated crystals were separated from the solution with a method such as a filtration method and a centrifugal separation method, were washed and dried to provide pentacene of high purity. In such a purifying method, pentacenequinone (quinone compound) of an impurity of pentacene remains in the solution because of having high solubility to an organic compound which is a solvent.

By the way, a crystal can be largely grown when a crystal of pentacene is precipitated. It is also possible to more highly purify the pentacene by repeating such a purifying step as described above several times. Furthermore, it is possible to highly purify a condensed polycyclic aromatic compound by introducing the condensed polycyclic aromatic compound solution into a column having temperature gradient, and by making the crystal continuously and repeatedly precipitate and dissolve in the solution in the column.

A condensed polycyclic aromatic compound highly purified with such a purifying method contains 1 mass % or less of a quinone compound (quinone body of condensed polycyclic aromatic compound) which is an impurity. By using a condensed polycyclic aromatic compound of such high purity, it becomes possible to prepare an organic semiconductor device showing high performance.

The lower is preferably the content of a quinone compound, the higher is the performance of an organic semiconductor device. Accordingly, the content is preferably 1 mass % or less, is more preferably 0.5 mass % or less, and is further preferably 0.2 mass % or less. By the way, there may be a case where a quinone body cannot be formed though it depends on a skeleton structure of a condensed polycyclic aromatic compound. In the case of such a condensed polycyclic aromatic compound, the compound with a structure containing a carbonyl group shall be an impurity corresponding to the quinone compound.

By applying such a purifying method, it is possible to prevent impurities from contaminating the condensed polycyclic aromatic compound thin film in the step of forming the thin film from a condensed polycyclic aromatic compound solution and to form the thin film made of the high-purity condensed polycyclic aromatic compound. Specifically, in a process of forming the thin film from the condensed polycyclic aromatic compound solution, the condensed polycyclic aromatic compound precipitates first and impurities such as a quinone compound are concentrated in the solution, because the impurities have high solubility to an organic compound corresponding to a solvent in the condensed polycyclic aromatic compound solution. Other methods for forming the thin film of the high-purity condensed polycyclic aromatic compound includes, for instance, a method of removing a liquid phase in which the impurities are concentrated in the process of forming the thin film from the condensed polycyclic aromatic compound solution, or a method of contacting a formed thin film with the organic compound (solvent) capable of dissolving the impurities in itself and extracting the impurities into the organic compound.

The content of impurities in a condensed polycyclic aromatic compound can be quantified by measuring a spectrum of a solution having the condensed polycyclic aromatic compound dissolved therein. Many of the condensed polycyclic aromatic compounds are hardly soluble, in other words, have extremely low solubility at room temperature, so that the case of having quantified the impurities with the use of the solution has not previously been reported. The present inventors have found a method of dissolving the condensed polycyclic aromatic compound in a solvent to form a solution, and that it is easily possible to measure the purity of the condensed polycyclic aromatic compound through measuring the spectrum of the solution. Conventionally, the method for measuring the purity of the condensed polycyclic aromatic compound was not clear, so that the purity was not measured except the case of measuring the purity with a gravimetric analysis method.

In the next place, an example will be shown in which the purity of pentacene has been measured through measuring the spectrum of a solution as described above. A pentacene solution is prepared by dissolving pentacene in trichlorobenzene (corresponding to solvent) of an organic compound capable of dissolving pentacene, and is subjected to the measurement of, for instance, the absorption spectrum in a range of visible light to ultraviolet light. Then, a content of pentacene quinone in pentacene can be quantified from a ratio of the absorption intensity of pentacene in a characteristic absorption band of 580 nm (absorption coefficient of trichlorobenzene: 330) to the absorption intensity of pentacene quinone which is an impurity, in a characteristic absorption band of 400 nm (absorption coefficient of trichlorobenzene: 9,900).

An absorption position and absorption coefficient of a characteristic absorption band of a pentacene derivative change depending on a type of a substituent and a substitution position, but the pentacene derivative can be quantified as in the case of pentacene. The absorption position of the characteristic absorption band for a quinone body of the pentacene derivative changes a little due to substitution by the substituent, and the characteristic absorption band exists within a range of 390 to 420 nm. The absorption coefficient also shows a value as high as that of pentacene quinone. Thus, the absorption position of the characteristic absorption band of the quinone body of the pentacene derivative exists in a lower range than the absorption position of the characteristic absorption band of the pentacene derivative, and the absorption coefficient of the quinone body of the pentacene derivative is high, so that a content of the quinone body of the pentacene derivative can be quantified with high accuracy.

The content of impurities can be quantified not only by an absorption spectrum in a range of visible light to ultraviolet light, but also by another spectrum such as a fluorescence spectrum and an infrared absorption spectrum.

In the next place, an organic compound to be used for forming a solution of a condensed polycyclic aromatic compound will be described. The organic compound to be used in the present invention needs to have a higher vapor pressure than that of the condensed polycyclic aromatic compound. The organic compound preferably can dissolve the condensed polycyclic aromatic compound at a higher temperature than ordinary temperature, and can form a homogeneous solution. Such an organic compound includes at least one compound of halogenated hydrocarbon and hydrocarbon.

The halogenated hydrocarbon includes, for instance, aromatic halogenated hydrocarbon such as chlorobenzene, bromobenzene, iodobenzene, fluorobenzene, dichlorobenzene, dibromobenzene, diiodobenzene, difluorobenzene, trichlorobenzene, chlorotoluene, bromotoluene, iodotoluene, dichlorotoluene, dibromotoluene, difluorotoluene, chloroxylene, bromoxylene, iodoxylene, chloroethylbenzene, bromoethylbenzene, iodoethylbenzene, dichloroethylbenzene, dibromoethylbenzene, chloronaphthalene, bromonaphthalene, dichloronaphthalene, dichloroanthracene, tetrachlorobenzene, tribromobenzene and tetrabromobenzene; and aliphatic halogenated hydrocarbon such as dichloroethane, trichloroethane, difluoroethane, tetrachloroethane, tetrafluoroethane, fluorochloroethane, chloropropane, dichloropropane, chloropentane, chlorohexane and chlorocyclopentane.

The hydrocarbon includes, for instance, aromatic hydrocarbon such as toluene, xylene, mesitylene, naphthalene, methylnaphthalene and tetralin; and aliphatic hydrocarbon such as decahydronaphthalene, octane, nonane, decane, undecane, dodecane and cycloheptane. The hydrocarbon further includes an ether such as diphenyl ether; a carbonate such as propylene carbonate; an ester (such as butyl lactone and propiolactone); a ketone (such as cyclohexanone and methyl isobutyl ketone); and a sulfone (such as dimethyl sulfoxide and diphenyl sulfone).

Among the organic compounds, an aromatic halogenated hydrocarbon is preferable when considering a degree of the solubility of a condensed polycyclic aromatic compound and properties of a formed thin film. The organic compound preferably has a boiling point of 100° C. or higher, in order to heat a mixture to a higher temperature than ordinary temperature and dissolve the condensed polycyclic aromatic compound in the organic compound to form a solution. Furthermore, the organic compound preferably has a boiling point of 250° C. or lower, because the organic compound needs to have a higher vapor pressure than that of the condensed polycyclic aromatic compound in order to remove the organic compound from the mixture to form the thin film. When the solution is prepared under a high pressure, the boiling point of the organic compound is not limited in particular.

It is acceptable to employ one type of the organic compound singly or a mixture of two or more types of the organic compounds. For instance, by employing a mixture of two or more types of the organic compounds, the surface energy of the organic compound and the dielectric constant of a condensed polycyclic aromatic compound solution can be adjusted, and thus, it becomes possible to adjust a spreadability or wettability of the solution necessary when spreading the condensed polycyclic aromatic compound solution on a base and vaporizing the organic compound. It is also possible to adjust the spreadability or wettability of the solution necessary when spreading the condensed polycyclic aromatic compound solution on a base and to reduce defects of the condensed polycyclic aromatic compound thin film also by appropriately adding an additive such as a surface active agent, an antifoaming agent and a thickener to the condensed polycyclic aromatic compound solution.

In the next place, a method for preparing a condensed polycyclic aromatic compound thin film by a wet process from a mixture (liquid dispersion or homogeneous solution) containing the condensed polycyclic aromatic compound and the organic compound as described above will be described.

The condensed polycyclic aromatic compound thin film is formed on a base by spreading a mixture containing the condensed polycyclic aromatic compound and the organic compound on the base, and heating the mixture to a higher temperature than ordinary temperature, because the organic compound and the solvent subsequently vaporize from the heated mixture due to the heat and are removed from the mixture. However, when the above described mixture is a liquid dispersion (in which the condensed polycyclic aromatic compound is dispersed in the solvent), at least a part of the condensed polycyclic aromatic compound in the mixture is dissolved in the solvent, and then the organic compound and the solvent are removed from the mixture.

It is acceptable to arrange a solution obtained by heating the above described mixture to a higher temperature than ordinary temperature on a heated base, and vaporize an organic compound and a solvent to form a thin film. Thus, a method for preparing a condensed polycyclic aromatic compound thin film needs to include the step of heating a mixture containing the condensed polycyclic aromatic compound and the organic compound to a higher temperature than ordinary temperature to form the solution. Accordingly, it is possible to adopt a method of, for instance, sequentially supplying the condensed polycyclic aromatic compound and the organic compound capable of dissolving the compound separately at a higher temperature than ordinary temperature onto the base to form the mixture, heating the mixture to form the solution, and vaporizing the organic compound and the solvent to form the condensed polycyclic aromatic compound thin film.

Among the methods for preparing the condensed polycyclic aromatic compound thin film, a preferable one is the method of spreading a solution formed by heating the above described mixture on a heated base and vaporizing the organic compound and the solvent to form the condensed polycyclic aromatic compound thin film, because thus formed condensed polycyclic aromatic compound thin film is excellently homogeneous. When the above described mixture is heated to form the solution, it is acceptable that some condensed polycyclic aromatic compounds remain as a solid, but it is preferable that the mixture forms a homogeneous solution free from the solid.

A content of an organic compound in the whole mixture is preferably 30 mass % or more but 99.9 mass % or less. When the content is less than 30 mass %, a condensed polycyclic aromatic compound in the mixture does not sufficiently dissolve in the organic compound, which is not preferable. An upper limit of the content of the organic compound is 99.9 mass %, because the content of the condensed polycyclic aromatic compound is preferably more than 0.1 mass % in order to form an adequate thin film.

An operation for preparing a thin film such as the preparation of the above described mixture, heating, the supply of the above described mixture onto a base and the vaporization of an organic compound can be ordinarily performed under atmospheric air or an inert gas atmosphere such as nitrogen gas and argon gas, though depending on a structure of a condensed polycyclic aromatic compound. However, when employing pentacene or a pentacene derivative to prepare a thin film with high mobility, it is preferable to perform the operation under the atmosphere of an inert gas.

In addition, it is preferable to control a heating temperature (a temperature at which a condensed polycyclic aromatic compound is dissolved in a solvent containing the above described organic compound) for the above described mixture to 60° C. or higher but 250° C. or lower. When the heating temperature is lower than 60° C., the condensed polycyclic aromatic compound becomes less soluble in the solvent, and tends to form a discontinuous thin film of it. In addition, when the temperature of a base (substrate) is as low as ordinary temperature, crystals may be produced when the above described mixture is spread over the base and may float in the mixture, which hardly forms a continuous condensed polycyclic aromatic compound thin film. On the other hand, when the heating temperature exceeds 250° C., the organic compound capable of dissolving the condensed polycyclic aromatic compound in it tends to easily vaporize, which hardly forms a uniform condensed polycyclic aromatic compound thin film. Furthermore, such a high heating temperature may cause a problem in a process, for example, the above described mixture is conveyed and the mixture is spread onto the base only in a non-uniform manner, because the solid condensed polycyclic aromatic compound rapidly precipitates. In order to inhibit such problems, the temperature of the above described heated mixture is controlled at preferably to 70° C. or higher but 240° C. or lower, further preferably to 80° C. or higher but 230° C. or lower, and most preferably to 100° C. or higher but 220° C. or lower.

A method for spreading a mixture containing a condensed polycyclic aromatic compound on a base such as a substrate includes an application method, a spraying method, and further a method of contacting the base with the above described mixture. Specifically, the method includes a well-known method such as a spin coating method, a dip coating method, a spouting method, a screen printing method, an ink-jet printing method, a blade coating method and a printing method (planographic process, intaglio printing and letterpress printing).

It is preferable to heat the mixture containing a condensed polycyclic aromatic compound to a higher temperature than ordinary temperature, arrange it on a base by the above-mentioned method, and heat the base. The temperature of the heated base is preferably 60° C. or higher but 230° C. or lower, more preferably is 70° C. or higher but 220° C. or lower, and further preferably is 80° C. or higher but 210° C. or lower. The temperature out of the above range tends to cause a problem that the condensed polycyclic aromatic compound thin film is ununiformly formed or a problem in a process, according to the same reason as in the heated mixture.

A mixture spread over a base and the base may be controlled to the same temperature or different temperatures. As a result of having examined correlation between the heating temperature and the form of crystals produced on the surface of the base, it was found that a supercooling degree when the crystals of a condensed polycyclic aromatic compound precipitated from the solution of the condensed polycyclic aromatic compound affected a precipitation behavior of the crystals. Specifically, an extremely high supercooling degree accelerates the formation of many crystal nuclei, easily forms separated crystals in the condensed polycyclic aromatic compound thin film, and causes an adverse effect of making the grain boundaries of the crystals hinder the transportation of electrons and holes. When the base is heated to the above described temperature range, the supercooling degree is decreased and the uniform condensed polycyclic aromatic compound thin film tends to be easily formed. However, when the base is heated too much, micro crystallites of the condensed polycyclic aromatic compound precipitate from a mixture, which may degrade the homogeneity in the condensed polycyclic aromatic compound thin film. The above phenomenon is considered to occur due to an increased supercooling degree of the mixture by the vaporization of the above described organic compound.

For this reason, in order to form the condensed polycyclic aromatic compound thin film of high quality, it is recommended to control a value obtained by subtracting a temperature of a base from a temperature of a mixture preferably to −15° C. or higher but 190° C. or lower, more preferably to 0° C. or higher but 100° C. or lower, and further preferably to 0° C. or higher but 80° C. or lower.

It is preferable to set a temperature of a mixture equal to or higher than a temperature of a base, but it was also found that even when the temperature of the mixture was set at a slightly lower temperature than the base temperature, a semiconductor thin film of high quality was formed. In the present invention, the temperature of the mixture and the temperature of the base indicate the temperatures when both are contacted with each other. When the mixture in a slightly lower temperature than the temperature of the base is heated by the base after having been spread over the base, the mixture is considered to pass through a state in which supersaturation is moderated and form an organic semiconductor thin film while keeping a supersaturated state caused by the vaporization of an organic compound and a solvent.

It is not preferable for a temperature of a mixture to be much higher than the temperature of a base, because many micro crystallites of a condensed polycyclic aromatic compound precipitate. It is not preferable also for a temperature of the base to be much higher than the temperature of the mixture, because crystals of the condensed polycyclic aromatic compound precipitate in a liquid phase or on a gas-liquid interface spread over the base, and degrade the quality of the thin film such as thickness uniformity and transporting properties. For this reason, it is preferable to keep the temperature of the mixture equal to or higher than the temperature of the base.

A supercooling degree is a motive force for producing the condensed polycyclic aromatic compound thin film from a mixture, so that it is not preferable for the supercooling degree to be extremely low, because the condensed polycyclic aromatic compound thin film is formed at a low speed to lower the productivity. Accordingly, it is necessary to adjust the supercooling degree of the mixture, in order to form a uniform thin film of high quality of the condensed polycyclic aromatic compound.

As described above, the condensed polycyclic aromatic compound thin film according to the present invention can be prepared in a wet process. Therefore, the thin film can be prepared more easily and in a shorter time than a conventional vacuum process, and accordingly with high productivity and at a low cost. According to the present invention, the condensed polycyclic aromatic compound thin film which has been considered to be insoluble or hardly soluble can be prepared in the wet process, and accordingly can increase the number of materials which can be prepared by the wet process.

In addition, the condensed polycyclic aromatic compound thin film and an organic semiconductor device having higher performance can be prepared by using the above described high-purity condensed polycyclic aromatic compound, when preparing the condensed polycyclic aromatic compound thin film by using the above described mixture containing the condensed polycyclic aromatic compound with the above described method for preparing a condensed polycyclic aromatic compound thin film.

Various materials can be used for a material of a base for forming the condensed polycyclic aromatic compound thin film thereon. The material includes, for instance, a ceramic material such as glass, quartz, aluminum oxide, magnesium oxide, silicon, gallium arsenic, indium-tin oxide (ITO), zinc oxide and mica; and a metal such as aluminum, gold, stainless steel, iron and silver. The material also includes a resin such as a polyester (polyethylene terephthalate, polybutylene terephthalate, polyethylene naphthalate and the like), a polycarbonate, a norbornene resin, polyether sulfone, polyimide, polyamide, cellulose, a silicone resin and an epoxy resin; carbon and paper. Alternatively, a composite of them is also acceptable. However, when the base is swollen by or is dissolved in an organic compound and causes troubles, the base preferably has a barrier layer for inhibiting the organic compound from diffusing into it thereon. Alternatively, it is possible to modify the surface of the base with a material having a suitable surface energy, so as to match the surface energy with that of the condensed polycyclic aromatic compound thin film and adjust the wettability of a mixture to the base.

The shape of a base is not limited in particular, but normally, a film-shaped base or a tabular base (substrate) is used. In addition, a solid such as a rectangular solid and a solid sphere can be used as the base. Furthermore, a filament and a fiber structure can be used as the base.

Thus prepared condensed polycyclic aromatic compound thin film has high crystallinity, and has a structure in which molecules of a condensed polycyclic aromatic compound orient so that the major axes orient in a perpendicular direction to the surface of the thin film or the surface of a base. Among diffraction peaks of (00n) planes (where n is an integer of 1 or larger) in a wide angle x-ray diffraction pattern, a diffraction peak for the (001) plane has a half peak width of 0.05 degrees or more but 0.2 degrees or less. This means that a crystal in the thin film is largely grown, and consequently that the thin film has superior semiconductor characteristics.

Furthermore, thus prepared pentacene thin film has high crystallinity, and has a structure in which pentacene molecules orient so that the major axes orient in a perpendicular direction to the surface of the thin film or the surface of a base. Particularly, the crystal structure of the thin film is different from the structure of the thin film formed by a vacuum deposition method which is a general method for forming the thin film.

A pentacene thin film formed by a vacuum deposition method has a crystal structure which is mainly formed of so-called a thin film phase (having an interplanar distance between (001) diffraction planes of 1.50 to 1.53 nm) containing such molecules as the major axes orient in a direction approximately perpendicular to the surface of a base, and makes the stabilized bulk phase (with an interplanar distance of 1.40 to 1.45 nm) partially coexist in it. Such a pentacene thin film has high crystallinity, but has a structure formed of metastable crystals, and accordingly has not a stable crystal structure.

In contrast to this, a pentacene thin film prepared by a method according to the present invention has a different crystal structure from that formed by a vacuum deposition method, is formed only of a stabilized bulk phase, and accordingly has a highly stable crystal structure. Specifically, the pentacene thin film according to the present invention shows a wide angle x-ray diffraction pattern in which most of diffraction peaks existing therein are diffraction peaks for a (001) plane corresponding to an interplanar distance of 1.4 nm or more but less than 1.5 nm, and diffraction peaks for the (001) plane corresponding to an interplanar distance of 1.5 nm or more but less than 1.6 nm are very small. In addition, a ratio (I)/(I') of the intensity (I) of a diffraction peak for a (001) plane corresponding to an interplanar distance of 1.4 nm or more but less than 1.5 nm to the intensity (I') of a diffraction peak for a (001) plane corresponding to an interplanar distance of 1.5 nm or more but less than 1.6 nm exceeds 10.

In addition, the pentacene thin film according to the present invention shows diffraction peaks for (00n) planes (where n is an integer of 1 or larger) of higher order than the pentacene thin film obtained by a vacuum deposition method, because of having high crystallinity.

Furthermore, the pentacene thin film according to the present invention shows the diffraction peak pattern in which the diffraction peak for a (001) plane among the diffraction peaks of (00n) planes (where n is an integer of 1 or larger) corresponding to an interplanar distance of 1.4 nm or more but less than 1.5 nm has a half peak width of 0.08 degrees or more but 0.2 degrees or less. The small half peak width of the diffraction peak shows that crystals in the thin film have large sizes, which leads to superior semiconductor characteristics of the pentacene thin film because the large crystals reduce an effect caused by the grain boundaries. Here, the above described half peak width is preferably 0.05 degrees or more but 0.2 degrees or less.

Furthermore, a method for preparing a thin film according to the present invention can largely grow a crystal in comparison with a conventional vacuum deposition method. The form of a thin film can be distinguished through an atomic force microscope (AFM), an electron microscope and an optical microscope.

The pentacene thin film according to the present invention shows the form (structure of crystal) of partially having a structure consisting of particulate crystals, and also having a structure consisting of a plate crystal and a sheet-shaped structure formed of the plate crystal that has grown widely on the surface of a base. The structure consisting of the plate crystals and the sheet-shaped structure are not observed in the pentacene thin film formed by a vacuum deposition method, and are the structure peculiar to the pentacene thin film obtained by a method according to the present invention for preparing the thin film. The sheet-shaped structure in the pentacene thin film according to the present invention shows a comparatively flat surface, a step part of the crystal, which is linear in parallel and is formed in the same plane, and almost no grain boundary structure.

As a result of having prepared field-effect transistors by using the thin films of pentacene having the above each structure and having compared their performances, it was found that a transistor provided with the pentacene thin film having a structure consisting of a plate crystal and a sheet-shaped structure in a channel was superior in properties such as an electric field-effect mobility and threshold voltage stability to the transistor provided with the pentacene thin film having a structure consisting of particulate crystals in the channel. Particularly, the transistor provided with the pentacene thin film having the sheet-shaped structure in the channel has preferable properties such as a high on-current, asymptotic threshold voltage approaching to 0 V and a high on/off current ratio.

A transistor provided with a pentacene thin film according to the present invention has a higher on/off current ratio and a lower threshold voltage than the transistor provided with the pentacene thin film formed by a normal vacuum deposition method. The transistor provided with the pentacene thin film according to the present invention, for instance, has such a high performance as an on/off current ratio of $1 \times 10^4$ or higher and such an excellent performance as a threshold voltage of 5 V to −5 V. When the transistor is used for a TFT of a display device, the formed device can display an image of high definition due to the high on/off current ratio. In addition, the transistor consumes little power, because of reduced low operating voltage of TFT due to the low threshold voltage.

In a pentacene thin film according to the present invention, a plate crystal grows into a size of 3 μm or larger by a particle size, and grows into a sheet-shaped structure with the size of several millimeters to several centimeters though depending on a thin-film-forming condition. Furthermore, it is possible to prepare a thin film close to a single crystal, in which the sheet-shaped crystal grows all over the surface of a base. When the pentacene thin film consists of large plate crystals or large sheet-shaped structures as described above, an organic semiconductor device prepared with the use of the thin film shows uniform transport properties of high performance, which is preferable.

When a condensed polycyclic aromatic compound is pentacene, the quality of a formed condensed polycyclic aromatic compound thin film can be evaluated, for instance, as described below. Specifically, the quality can be evaluated by forming a field-effect transistor with the use of the condensed polycyclic aromatic compound thin film, and by measuring the electric field-effect mobility. The electric field-effect mobility is preferably 0.1 cm$^2$/V·s or more, more preferably is 0.5 cm$^2$/V·s or more, and further preferably is 1 cm$^2$/V·s or more.

In addition, a threshold voltage determined from a gate voltage dependency of a drain current in a field-effect transistor tends to draw an asymptote approaching to zero, and the condensed polycyclic aromatic compound thin film according to the present invention formed on a base by heating the mixture has the preferable characteristics. The reason why the transistor shows high mobility and the low threshold voltage is not clear, but it is conceivable that crystals have largely grown in the condensed polycyclic aromatic compound thin film and have reduced grain boundaries among the crystals. The transistor shows more adequate characteristics by using the condensed polycyclic aromatic compound thin film, for instance, pentacene according to the present invention than the case of using the film formed by a normal vapor deposition method.

It is possible to prepare a semiconductor device useful in fields of electronics, photonics, bioelectronics and the like by using the condensed polycyclic aromatic compound thin film. Such a semiconductor device includes, for instance, a diode, a transistor, a thin film transistor, a memory, a photodiode, a light-emitting diode, a light-emitting transistor and a sensor.

A transistor and a thin film transistor can be used in a display, and accordingly can be used in various display devices such as a liquid crystal display, a dispersion type liquid crystal display, an electrophoretic display unit, a particle rotation type display device, an electrochromic display, an organic luminescent display, an electronic paper and the like. The transistor and the thin film transistor are used in a transistor for switching a display pixel, a signal-driver circuit element, a memory circuit element and a signal-processing circuit element of those display devices.

When a semiconductor device is a transistor, the structure of the device includes, for instance, the structure of substrate/gate electrode/insulator layer (dielectric layer)/source electrode–drain electrode/semiconductor layer; the structure of substrate/semiconductor layer/source electrode–drain electrode/insulator layer (dielectric layer)/gate electrode; and the structure of substrate/source electrode (or drain electrode)/semiconductor layer+insulator layer (dielectric layer)+gate electrode/drain electrode (or source electrode). At this time, a plurality of the source electrodes, the drain electrodes and the gate electrodes may be arranged respectively. In addition, a plurality of semiconductor layers may be arranged in the same plane or may be stacked.

The transistor can adopt any configuration of an MOS (metal-oxide (insulator layer)-semiconductor) type and a bipolar type. A condensed polycyclic aromatic compound is normally a p-type semiconductor, and accordingly can constitute a device by combining it with a condensed polycyclic aromatic compound doped with a donor to form an n-type semiconductor, or combining it with the n-type semiconductor other than the condensed polycyclic aromatic compound.

On the other hand, when a semiconductor device is a diode, the structure of the device includes, for instance, the structure of electrode/n-type semiconductor layer/p-type semiconductor layer/electrode. At this time, the condensed polycyclic aromatic compound thin film according to the present invention is used for the p-type semiconductor layer, and the above described n-type semiconductor is used for the n-type semiconductor layer.

At least one part of a joint surface of the inner part of the condensed polycyclic aromatic compound thin film or the surface of the condensed polycyclic aromatic compound thin film in a semiconductor device with an electrode can be a Schottky joint and/or a tunnel joint. The semiconductor device having such a joint structure is preferable because it can be used for preparing a diode and a transistor with a simple structure. In addition, the organic semiconductor device having such a joint structure can form a device such as an inverter, an oscillator, a memory, a sensor and the like, by jointing a plurality of its own.

Furthermore, when a semiconductor device according to the present invention is used in a display device, it can be used as a transistor device (display TFT) which is distributed over respective pixels of a display device and switches the display of respective pixels. Such an active-drive display device does not need to form a pattern of a facing electroconductive substrate, and accordingly can simplify pixel wiring in comparison with a passive-drive display device having no transistor for switching the pixel, though it depends on a circuit configuration. A normal display has one or more switching transistors per pixel arranged therein. Such a display device has a structure composed of gate lines and data lines two-dimensionally intersected on the surface of a substrate, in which the data line and the gate line are connected to a gate electrode, a source electrode and a drain electrode of the transistor respectively. It is also possible to divide the data line from the gate line, or add a current-feed line and a signal line.

It is also possible to impart a function of recording a signal to a display device by further installing capacitors in pixels of a display device in addition to pixel wires and transistors. Furthermore, it is also possible to mount a driver for data lines and gate lines, a memory of the pixel signal, a pulse generator, a signal divider, a controller and the like on a substrate having the display device formed thereon.

An organic semiconductor device according to the present invention can be used in a computing device and a storage device in an integrated circuit card, a smart card and an electronic tag. In the case, the organic semiconductor device can be applied to either of a contact type or non-contact type of the above applications without any problem. The integrated circuit card, the smart card and the electronic tag are composed of a memory, a pulse generator, a signal divider, a controller and a capacitor, and may be further provided with an antenna and a battery.

Furthermore, an organic semiconductor device according to the present invention can be used in a diode, a device having a Schottky joint structure, and a device having a tunnel joint structure. Thus formed device can be used for; a light-receiving device such as a photoelectric transducer, a solar cell and an infrared sensor; a photodiode; and a light-emitting device as well. In addition, when the organic semiconductor device according to the present invention is used for forming a transistor, the transistor can be used as the light-emitting transistor. A light-emitting layer of the light-emitting devices can employ a well-known organic material and an inorganic material for its own material.

Furthermore, an organic semiconductor device according to the present invention can be used in a sensor, and can be applied to various sensors such as a gas sensor, a biosensor, a blood sensor, an immunosensor, an artificial retina and a taste sensor. The sensor can analyze a measurement object normally from a change in an ohmic value of the condensed polycyclic aromatic compound thin film, which occurs when the measurement object is contacted with or arranged adjacent to the condensed polycyclic aromatic compound thin film composing the organic semiconductor device.

In the next place, the present invention will be further specifically described with reference to examples.

<Example of Purifying Condensed Polycyclic Aromatic Compound>

A bluish purple homogeneous solution of pentacene was prepared by mixing 1 g of a pentacene powder (reagent made by Aldrich Corporation, which had been left unattended in atmosphere at ordinary temperature for about 5 years) with 300 g of 1,2,4-trichlorobenzene, and then heating the mixture to 180° C. in an atmosphere of nitrogen. A pentacene powder of high purity was obtained by cooling the solution to ordinary temperature to grow a crystal, filtering the precipitated crystal, and then by drying it with a vacuum dryer.

The powders of pentacene before and after having been refined were dissolved in 1,2,4-trichlorobenzene respectively, and solutions with the concentration of 0.1 g/L were prepared. The solutions were subjected to the measurement of an ultraviolet light-visible light absorption spectrum (in wavelength range of 300 nm to 900 nm). As a result of having determined the content of pentacene quinone from a ratio of the absorption intensity of pentacene quinone to the absorption intensity of pentacene, of which the absorption intensities were left values after having subtracted background from characteristic absorptions (respectively at 400 nm and at 580 nm), the content in the powder before refinement was 1.5 mass % and the content in the powder after refinement was 0.2 mass %.

Subsequently, a silicon substrate heavily doped with an n-type dopant (provided with an oxide layer with the thickness of 200 nm on its surface) was prepared and a pattern of a gold electrode was formed on the surface as a source/drain electrode. Then, a pentacene thin film was formed on the silicon substrate by a vacuum deposition method, and a transistor structure was formed. In the vacuum deposition process, pentacene was mounted on a tantalum boat and was vapor-deposited on the substrate by flash evaporation due to resistance heating.

A transistor was prepared by setting a silicon substrate as a gate electrode, a surface gold electrode as a source/drain electrode and a pentacene thin film as a semiconductor layer. Then, field-effect transistor characteristics were evaluated on the transistor. As a result, the transistor with the use of pentacene before being refined showed a mobility of 0.02 cm$^2$/V·s, an on/off current ratio of 1,000, and a threshold voltage of −25 V. On the other hand, the transistor with the use of pentacene after having been refined showed a mobility of 0.48 cm$^2$/V·s, an on/off current ratio of 5×10$^3$, and a threshold voltage of −15 V.

EXAMPLE 1

A bluish purple homogeneous solution of pentacene was prepared by mixing 30 mg of a pentacene powder (manufactured by Aldrich Corporation) with 30 g of 1,2,4-trichlorobenzene, and then heating the mixture to 120° C. in an atmosphere of nitrogen. A pentacene thin film (average film thickness of 200 nm) was formed on a silicon substrate, by spreading the pentacene solution on the substrate of 100° C. in an atmosphere of nitrogen and vaporizing 1,2,4-trichlorobenzene.

Thus obtained pentacene thin film showed a wide angle X-ray diffraction pattern (see FIG. 1) having the diffraction peaks for (00n) planes (n=1 to 6) corresponding to an interplanar distance of 1.45 nm and 1.42 nm, in which the diffraction peaks for the (001) planes among the above diffraction peaks showed a half peak width of 0.09 degrees and 0.07 degrees.

In the diffraction pattern, a diffraction peak for the (001) plane corresponding to an interplanar distance of 1.5 nm or more but less than 1.6 nm was not observed. Therefore, a ratio (I)/(I') of the intensity (I) of the diffraction peak for the (001) plane corresponding to the interplanar distance of 1.4 nm or more but less than 1.5 nm to the intensity (I') of the diffraction peak for the (001) plane corresponding to the interplanar distance of 1.5 nm or more but less than 1.6 nm exceeded 10 (was infinite).

As a result of having observed the structure of the obtained pentacene thin film with an AFM, a sheet-shaped structure formed of a plate crystal having grown up to several centimeters was observed. The structure partially formed of a plate crystal with the size of several micrometers was observed, but the structure formed of the particular crystal of a micrometer order was not observed.

Subsequently, a silicon substrate heavily doped with an n-type dopant (provided with an oxide layer with the thickness of 200 nm on its surface) was prepared and a pattern of a gold electrode was formed on the surface as a source/drain electrode. A transistor structure was prepared by heating the silicon substrate having such an electrode pattern formed thereon to 100° C., and spreading the above described pentacene solution on the substrate surface to form a pentacene thin film. A transistor was prepared by setting a silicon substrate as a gate electrode, a surface gold electrode as a source/drain electrode and a pentacene thin film as a semiconductor layer. Then, field-effect transistor characteristics were evaluated on the transistor. As a result, the transistor showed a mobility of 0.45 cm$^2$/V·s and an on/off current ratio of 1×10$^5$. The transistor also showed a threshold voltage of 1.0 V, which was determined from a curve drawn by the square root of a drain current and gate voltage.

EXAMPLE 2

A liquid dispersion having pentacene homogeneously dispersed therein was prepared by mixing 10 mg of a pentacene powder (manufactured by Aldrich Corporation) with 10 g of o-dichlorobenzene. Subsequently, the liquid dispersion of pentacene was spread onto a silicon substrate of 120° C. under an atmosphere of nitrogen. Then, pentacene dissolved in o-dichlorobenzene along with the rise of a temperature of the dispersion, and the pentacene dispersion was colored into bluish purple. Afterwards, o-dichlorobenzene vaporized and a pentacene thin film was formed on the surface of the silicon substrate.

Figure 2:
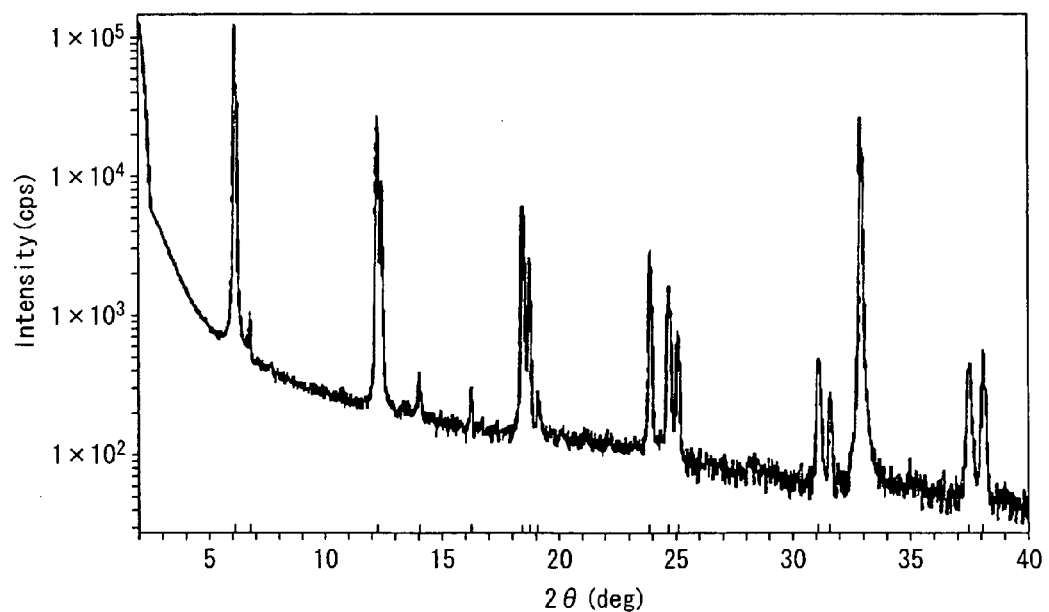
FIG. 2 is a view showing a wide angle X-ray diffraction pattern of a pentacene thin film in Example 2.

Thus obtained pentacene thin film showed a wide angle X-ray diffraction pattern (see FIG. 2) having the diffraction peaks for (00n) planes (n=1 to 5) corresponding to an interplanar distance of 1.45 nm and 1.44 nm, in which the diffraction peaks for the (001) planes among the above diffraction peaks showed a half peak width of 0.08 degrees and 0.06 degrees, respectively.

In the diffraction peak pattern, a diffraction peak for the (001) plane corresponding to an interplanar distance of 1.5 nm or more but less than 1.6 nm was not observed. Therefore, a ratio (I)/(I') of the intensity (I) of the diffraction peak for the (001) plane corresponding to the interplanar distance of 1.4 nm or more but less than 1.5 nm to the intensity (I') of the diffraction peak for the (001) plane corresponding to the interplanar distance of 1.5 nm or more but less than 1.6 nm exceeded 10 (was infinite).

As a result of having observed the structure of the obtained pentacene thin film with an AFM, a sheet-shaped structure formed of a plate crystal having grown up to several centimeters was observed. The structure partially formed of a plate crystal with the size of several micrometers was observed, but the structure formed of the particular crystal of a micrometer order was not observed.

Next, a transistor was prepared by heating the silicon substrate similar to that of Example 1 to 120° C., and spreading the above described pentacene dispersion on the substrate surface to form a pentacene thin film. As a result of having evaluated field-effect transistor characteristics by the same method as in the case of Example 1, the transistor showed a mobility of 0.25 cm$^2$/V·s, an on/off current ratio of 1×10$^5$, and a threshold voltage of 0.5 V.

EXAMPLE 3

A bluish purple homogeneous solution of pentacene was prepared by mixing 30 mg of a pentacene powder (manufactured by Aldrich Corporation) with 30 g of 1,2,4-trichlorobenzene, and then heating the mixture to 180° C. in an atmosphere of nitrogen. A pentacene thin film (with average film thickness of 100 nm) was formed on a silicon substrate, by spreading the pentacene solution on the substrate of 150° C. in an atmosphere of nitrogen and vaporizing 1,2,4-trichlorobenzene.

Figure 3:
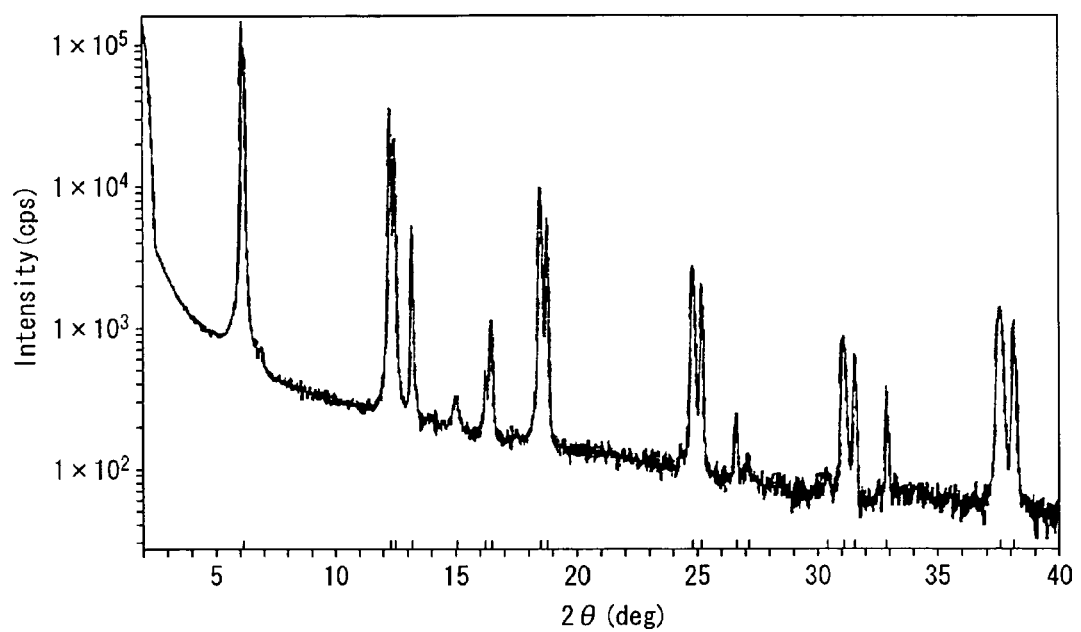
FIG. 3 is a view showing a wide angle X-ray diffraction pattern of a pentacene thin film in Example 3.

Thus obtained pentacene thin film showed a wide angle X-ray diffraction pattern (see FIG. 3) having the diffraction peaks for (00n) planes (n=1 to 6 or larger) corresponding to an interplanar distance of 1.48 nm and 1.43 nm, in which the diffraction peaks for the (001) planes among the above diffraction peaks showed a half peak width of 0.09 degrees and 0.07 degrees.

In the diffraction pattern, a diffraction peak for the (001) plane corresponding to an interplanar distance of 1.5 nm or more but less than 1.6 nm was not observed. Therefore, a ratio (I)/(I') of the intensity (I) of the diffraction peak for the (001) plane corresponding to the interplanar distance of 1.4 nm or more but less than 1.5 nm to the intensity (I') of the diffraction peak for the (001) plane corresponding to the interplanar distance of 1.5 nm or more but less than 1.6 nm exceeded 10 (was infinite).

As a result of having observed the structure of the obtained pentacene thin film with an AFM, a sheet-shaped structure formed of a plate crystal having grown up to several centimeters was observed. A structure partially formed of a plate crystal with the size of several micrometers was observed.

Figure 4:
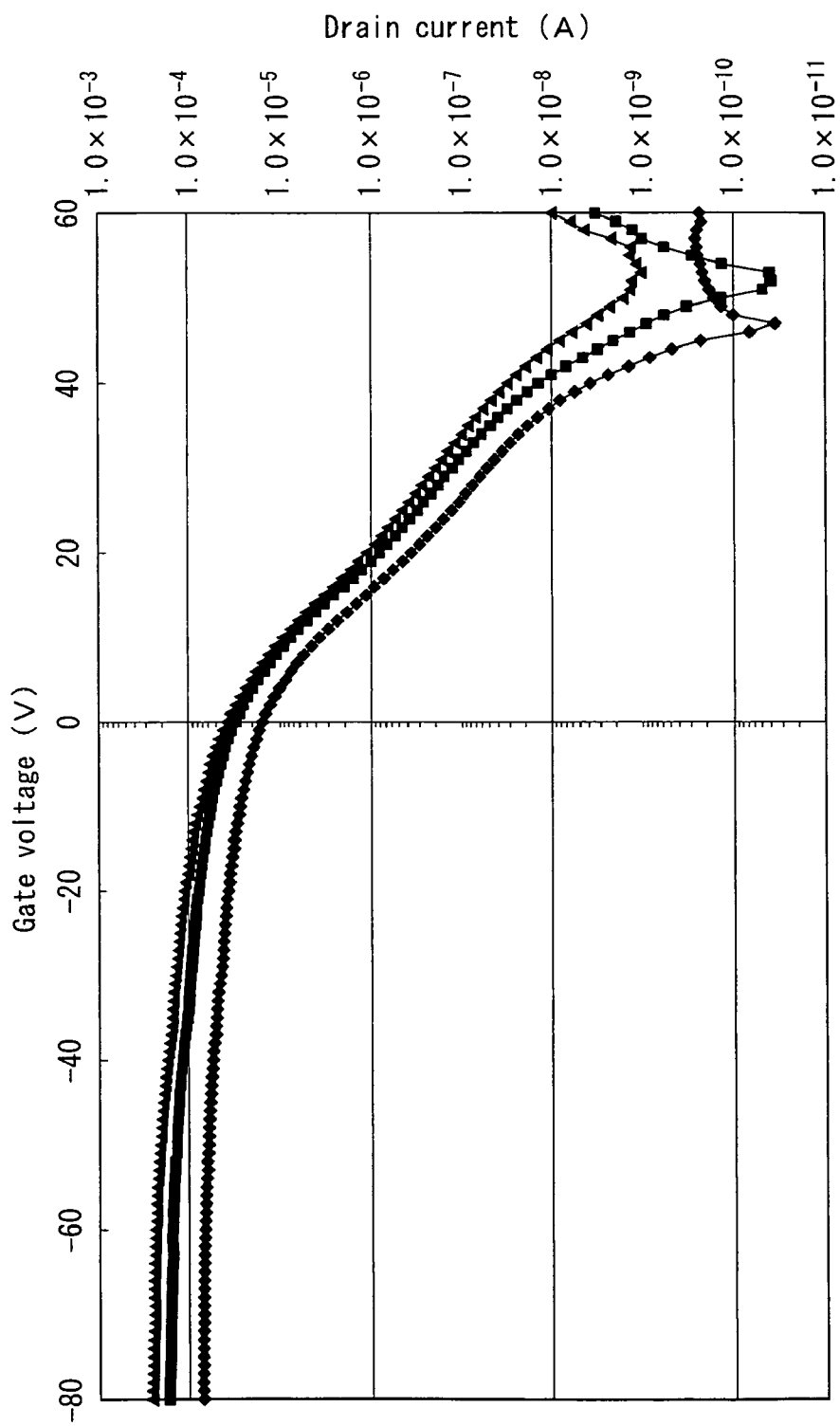
FIG. 4 is a view showing a curve of drain current/gate voltage of a transistor in Example 3.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 150° C., and spreading the above described pentacene solution on the substrate surface to form a pentacene thin film. A transistor was prepared by setting a silicon substrate as a gate electrode, a surface gold electrode as a source/drain electrode and a pentacene thin film as a semiconductor layer. Then, field-effect transistor characteristics were evaluated on the transistor. As a result, the transistor showed a mobility of 1.7 cm$^2$/V·s, an on/off current ratio of 1×10$^6$, and a threshold voltage of 4.1 V. For information, a curve of the drain current/gate voltage of a transistor in Example 3 is shown in FIG. 4.

EXAMPLE 4

Figure 5:
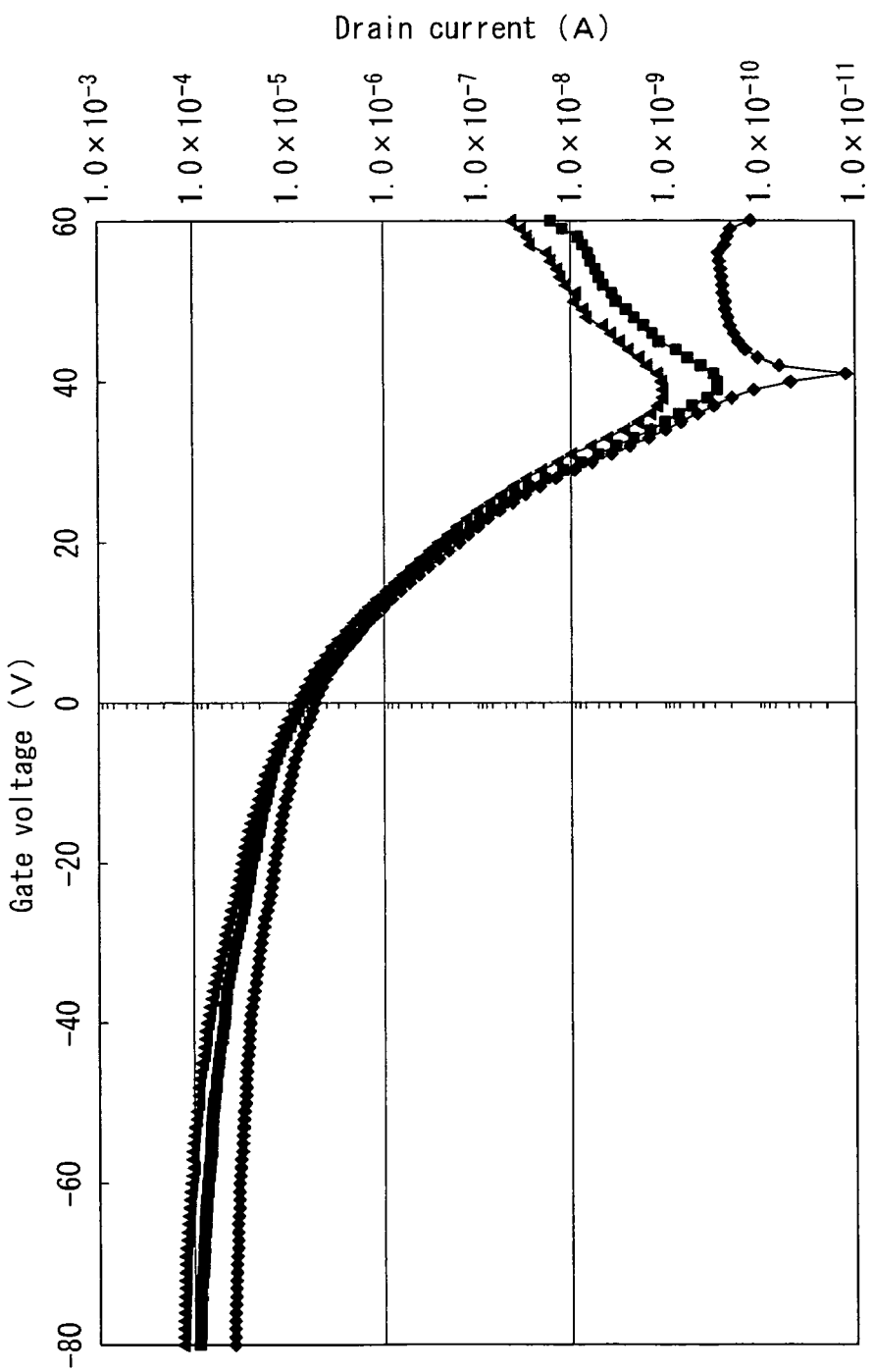
FIG. 5 is a view showing a curve of drain current/gate voltage of a transistor in Example 4.

A pentacene thin film was prepared by the same method as in the case of Example 3 except that the temperature of the silicon substrate was set at 175° C. Subsequently, a transistor was prepared with the use of the pentacene thin film by the same method as in the case of Example 3. As a result of having evaluated field-effect transistor characteristics, the transistor showed a mobility of 1.35 cm$^2$/V·s, an on/off current ratio of 1×10$^5$, and a threshold voltage of 3.3 V. For information, a curve of the drain current/gate voltage of a transistor in Example 4 is shown in FIG. 5.

EXAMPLE 5

A pentacene thin film was prepared by the same method as in the case of Example 3 except that the mixture of a pentacene powder and 1,2,4-trichlorobenzene was heated to 200° C. and the temperature of the silicon substrate was set at 140° C. Subsequently, a transistor was prepared with the use of the pentacene thin film by the same method as in the case of Example 3. As a result of having evaluated field-effect transistor characteristics, the transistor showed a mobility of 0.6 cm$^2$/V·s, an on/off current ratio of 1×10$^4$, and a threshold voltage of 0.8 V.

EXAMPLE 6

A pentacene thin film was prepared by the same method as in the case of Example 3 except that the temperature of the silicon substrate was set at 60° C. Subsequently, a transistor was prepared with the use of the pentacene thin film by the same method as in the case of Example 3. As a result of having evaluated field-effect transistor characteristics, the transistor showed a mobility of 0.12 cm$^2$/V·s, an on/off current ratio of 1×10$^5$, and a threshold voltage of −2.2 V. However, as a result of having observed the obtained pentacene thin film with a microscope, it was found that many fine particles of pentacene precipitated.

EXAMPLE 7

A homogeneous solution was prepared by mixing 10 mg of 2,3-dimethylpentacene with 10 g of o-dichlorobenzene, and then heating the mixture to 130° C. A thin film of 2,3-dimethylpentacene was formed on a silicon substrate, by spreading the solution on the substrate of 100° C. in an atmosphere of nitrogen and vaporizing o-dichlorobenzene.

Figure 6:
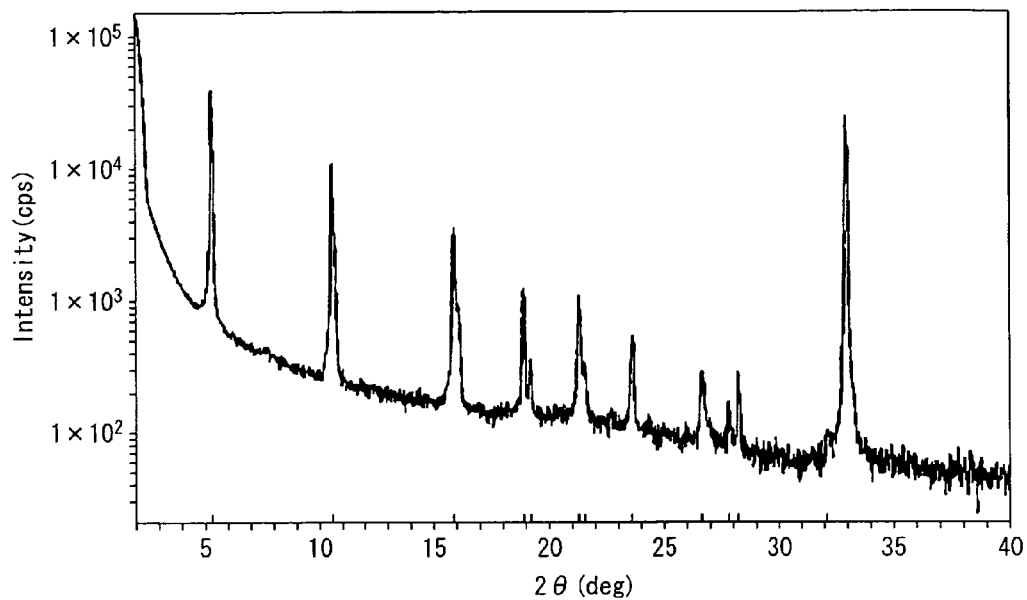
FIG. 6 is a view showing a wide angle X-ray diffraction pattern of a thin film of 2,3-dimethylpentacene in Example 7.

Thus obtained thin film of 2,3-dimethylpentacene showed a wide angle X-ray diffraction pattern (see FIG. 6) having the diffraction peaks for (00n) planes (n=1, 2, 3 and 4) corresponding to an interplanar distance (c-axis lattice constant) of 1.67 nm, in which the diffraction peaks for the (001) plane among the above diffraction peaks showed a half peak width of 0.08 degrees. The c-axis lattice constant was approximately equal to the sum (1.70 nm) of the length of a 2,3-dimethylpentacene molecule in a major axis direction and a van der Waals radius. Accordingly, it was found that the 2,3-dimethylpentacene molecule formed crystals in the thin film so that the major axes of the molecule were oriented perpendicular to the surface of the substrate.

Next, a transistor structure was prepared by heating the silicon substrate similar to that of Example 1 to 100° C., and spreading the above described solution of 2,3-dimethylpentacene on the substrate surface to form a thin film of 2,3-dimethylpentacene. As a result of having evaluated field-effect transistor characteristics by the same method as in the case of Example 1, the transistor showed a mobility of 1.25 $cm^2/V \cdot s$, an on/off current ratio of $1 \times 10^4$, and a threshold voltage of 4.6 V.

EXAMPLE 8

A homogeneous solution was prepared by mixing 10 mg of ovalene (manufactured by Dr. Ehrenstorfer GmbH) with 10 g of o-dichlorobenzene, and then heating the mixture to 130° C. A thin film of ovalene was formed on a silicon substrate, by spreading the ovalene solution on the substrate of 100° C. and vaporizing o-dichlorobenzene.

Figure 7:
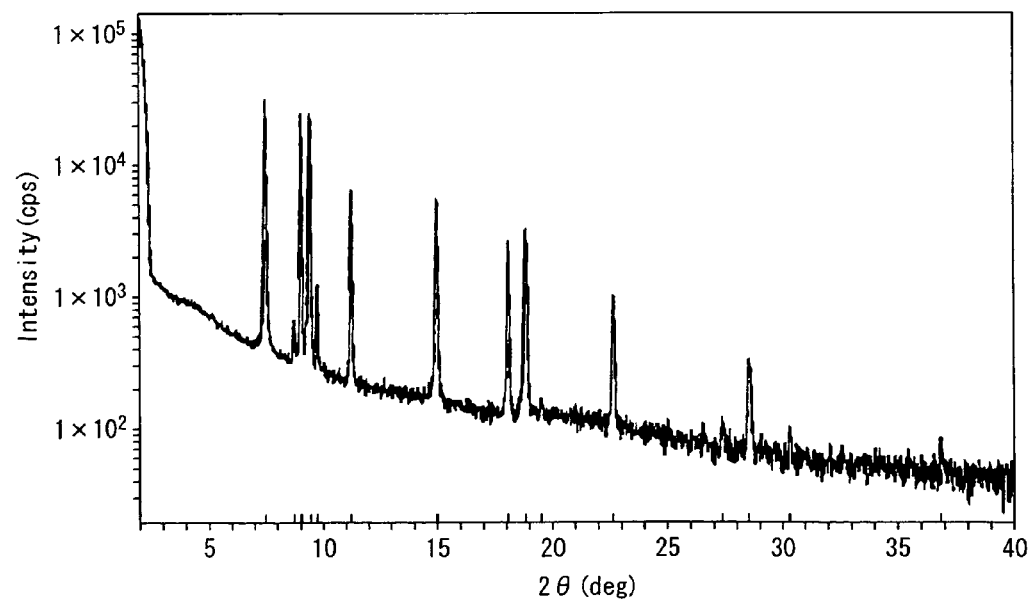
FIG. 7 is a view showing a wide angle X-ray diffraction pattern of a thin film of ovalene in Example 8.

Thus obtained thin film of ovalene showed a wide angle X-ray diffraction pattern (see FIG. 7) having the diffraction peaks for (00n) planes (n=1, 2, 3 and 4) corresponding to an interplanar distance (c-axis lattice constant) of 11.8 nm, in which the diffraction peaks for the (001) plane among the diffraction peaks showed a half peak width of 0.06 degrees. The interplanar distance of the (00n) planes was approximately equal to the length of an ovalene molecule in a major axis direction. Accordingly, it was found that the ovalene molecule formed crystals in the thin film so that the major axes of the molecule were oriented perpendicular to the surface of a substrate. For information, the diffraction peaks of (n00) faces and (20-2) faces were also observed in addition to the diffraction peaks of (00n) planes.

Figure 8:
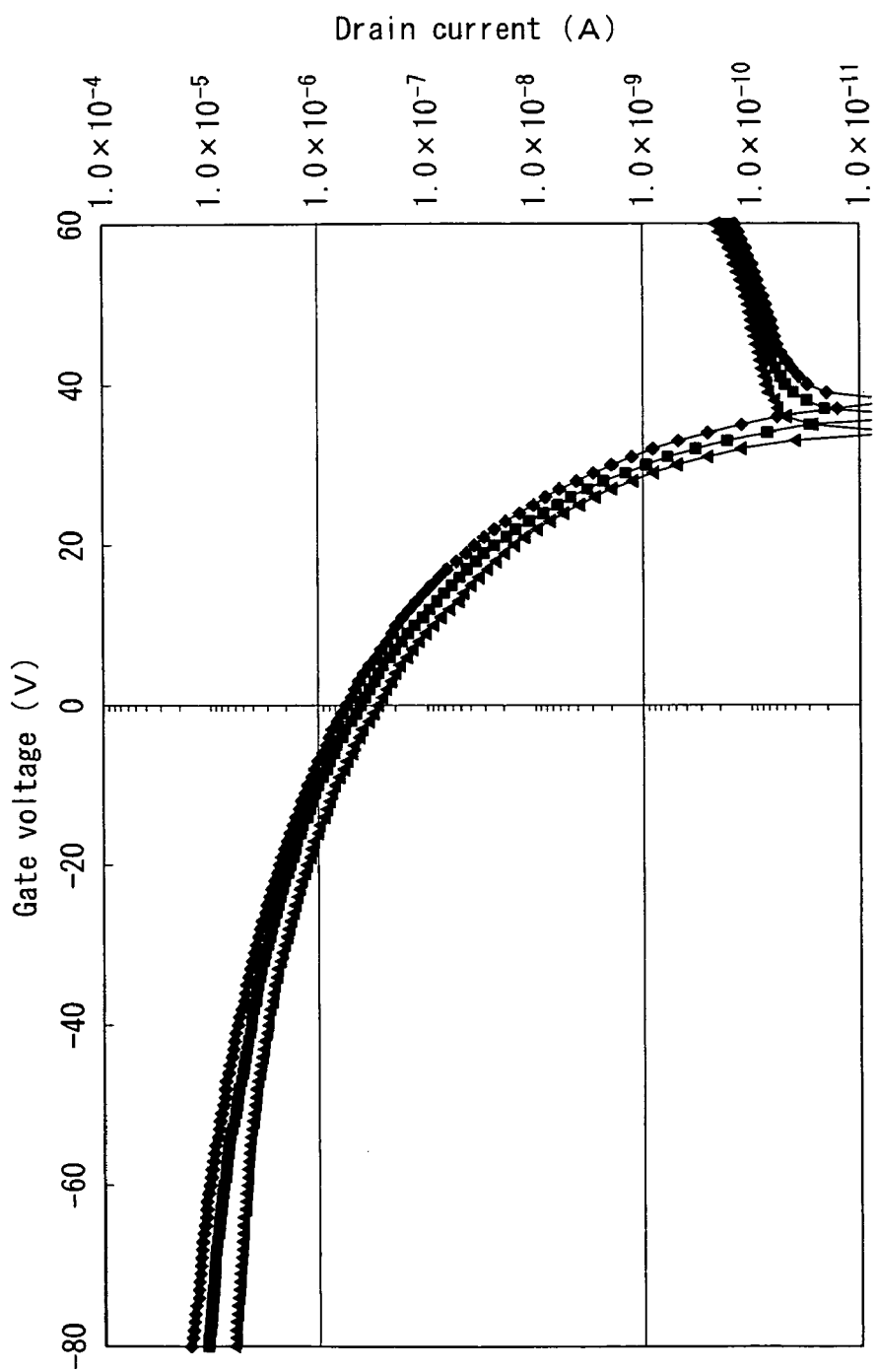
FIG. 8 is a view showing a curve of drain current/gate voltage of a transistor in Example 8.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 100° C., and spreading the above described ovalene solution on the substrate surface to form a thin film of ovalene. A transistor was prepared by setting a silicon substrate as a gate electrode, a surface gold electrode as a source/drain electrode and a thin film of ovalene as a semiconductor layer. Then, field-effect transistor characteristics were evaluated on the transistor. As a result, the transistor showed a mobility of 0.07 $cm^2/V \cdot s$, an on/off current ratio of $1 \times 10^5$, and a threshold voltage of 0.1 V. A curve of the drain current/gate voltage of a transistor in Example 8 is shown in FIG. 8.

On the other hand, the transistor provided with a vapor deposited film of ovalene showed a mobility of 0.03 $cm^2/V \cdot s$, an on/off current ratio of $1 \times 10^3$, and a threshold voltage of 35 V.

EXAMPLE 9

A homogeneous solution of tetracene was prepared by mixing 30 mg of tetracene (manufactured by Tokyo Chemical Industry Co., Ltd.) with 30 g of 1,2,4-trichlorobenzene, and then heating the mixture to 80° C. A thin film of tetracene was formed on a silicon substrate, by spreading the tetracene solution on the substrate of 80° C. and vaporizing 1,2,4-trichlorobenzene.

Figure 9:
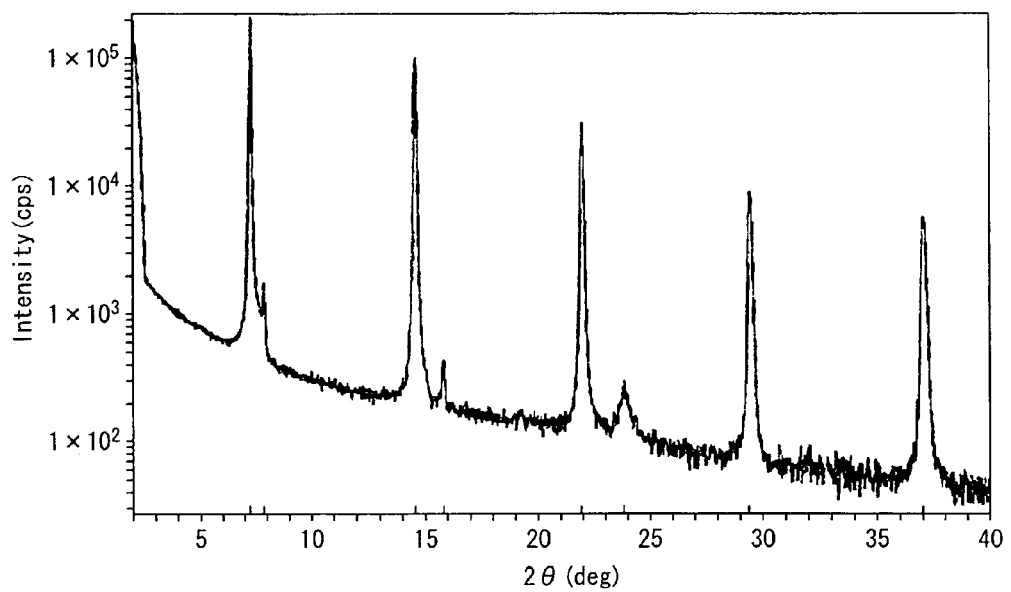
FIG. 9 is a view showing a wide angle X-ray diffraction pattern of a thin film of tetracene in Example 10.

A wide angle x-ray diffraction pattern (see FIG. 9) of an obtained thin film of tetracene had a diffraction peak of (00n) planes (n=1 to 6) corresponding to an interplanar distance (c-axis lattice constant) of 1.22 nm. Accordingly, it was found that the tetracene molecules formed crystals in the thin film so that the major axes of the molecules were oriented perpendicular to the surface of a substrate.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 100° C., and spreading the above described tetracene solution on the substrate surface to form a thin film of tetracene. A transistor was prepared by setting a silicon substrate as a gate electrode, a surface gold electrode as a source/drain electrode and a thin film of tetracene as a semiconductor layer. Then, field-effect transistor characteristics were evaluated on the transistor. As a result, the transistor showed a mobility of $6 \times 10^{-3}$ $cm^2/V \cdot s$, an on/off current ratio of $5 \times 10^3$, and a threshold voltage of 3.4 V. On the other hand, the transistor prepared with the use of the thin film of tetracene formed by a vacuum deposition method did not work as a transistor. As a result of having evaluated a structure of the vapor deposited film from a wide angle x-ray diffraction pattern, the diffraction pattern showed week diffraction intensity compared to that of the thin film of tetracene formed in the above described Example 9 and showed the diffraction peaks of (00n) planes, where n was only 1 to 3.

EXAMPLE 10

A compound tetradodecylhexabenzocoronene was synthesized by coupling bis (4-dodecylphenyl) acetylene with tetraphenyl cyclopentadienone by a Diels-Alder reaction, and then condensing the product by a Friedel-Crafts reaction.

A homogeneous solution was prepared by mixing 10 mg of the obtained tetradodecylhexabenzocoronene with 10 g of mesitylene, and then heating the mixture to 110° C. A thin film of tetradodecylhexabenzocoronene was formed on a silicon substrate, by spreading the solution on the substrate of 80° C. and vaporizing mesitylene.

Thus obtained thin film of tetradodecylhexabenzocoronene showed a wide angle X-ray diffraction pattern having the diffraction peaks for (00n) planes (n=1, 2 and 3) corresponding to an interplanar distance (c-axis lattice constant) of 22.1 nm, in which the diffraction peaks for the (001) plane among the above diffraction peaks showed a half peak width of 0.19 degrees. The interplanar distance of the (00n) plane was approximately 50% of the length of a tetradodecylhexabenzocoronene molecule in a major axis direction. Accordingly, it was found that the tetradodecylhexabenzocoronene molecules formed crystals in the thin film so that the molecule planes were oriented perpendicular to the surface of a substrate and the major axes of the molecules were otiented in parallel to the surface of a substrate.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 80° C., and spreading the above described tetradodecylhexabenzocoronene solution on the substrate surface to form a thin film of tetradodecylhexabenzocoronene. A transistor was prepared by setting a silicon substrate as a gate electrode, a surface gold electrode as a source/drain electrode and a thin film of tetradodecylhexabenzocoronene as a semiconductor layer. Then, field-effect transistor characteristics were evaluated on the transistor. As a result, the transistor showed a mobility of 0.05 $cm^2/V \cdot s$, an on/off current ratio of $1 \times 10^4$, and a threshold voltage of 5.4 V.

EXAMPLE 11

A compound of 2,3,9,10-tetramethylpentacene was obtained by coupling 1,5-dimethylbenzene-3,4-dialdehyde with cyclohexane-1,4-dione to synthesize 2,3,9,10-tetramethylpentacene-6,13-dione, and reducing and aromatizing it.

A homogeneous solution was prepared by mixing 20 mg of the 2,3,9,10-tetramethylpentacene with 10 g of 1,2,4-trichlorobenzene, and then heating the mixture to 150° C. in an atmosphere of nitrogen. A thin film of tetramethylpentacene was formed on a silicon substrate, by spreading the tetramethylpentacene solution on the substrate heated to 120° C. in an atmosphere of nitrogen and vaporizing trichlorobenzene.

Thus obtained thin film of tetramethylpentacene showed a wide angle X-ray diffraction pattern having the diffraction peaks for (00n) planes (n=1, 2, 3, 4, 5 and 6) corresponding to an interplanar distance of 1.82 nm, in which the diffraction peak for the (001) plane showed a half peak width of 0.05 degrees. The interplanar distance of the (00n) plane was approximately equal to the length of the tetramethylpentacene molecule, which is 1.8 to 1.9 nm. Accordingly, it was found that the major axes of tetramethylpentacene molecules were oriented perpendicular to the surface of a substrate.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 120° C., and spreading the above described tetramethylpentacene solution heated to 150° C. on the substrate surface to form a thin film of tetramethylpentacene. A transistor was prepared by setting a silicon substrate as a gate electrode, a surface gold electrode as a source/drain electrode and a thin film of tetramethylpentacene as a semiconductor layer. Then, field-effect transistor characteristics were evaluated on the transistor. As a result, the transistor showed a mobility of 1.6 $cm^2/V \cdot s$, an on/off current ratio of $1 \times 10^5$, and a threshold voltage of 1.8 V.

EXAMPLE 12

A compound of 2,3-dimethylpentacene was obtained by coupling 2,3-dimethylnaphthalene-6,7-dialdehyde with 1,4-dihydroxynaphthalene to synthesize 2,3-dimethylpentacene-6,13-dione, and reducing and aromatizing it.

A homogeneous solution was prepared by mixing 30 mg of 2,3-dimethylpentacene with 10 g of mesitylene (trimethylbenzene) in an atmosphere of nitrogen, and then heating the mixture to 150° C. A thin film of dimethylpentacene was formed on a silicon substrate, by spreading the dimethylpentacene solution on the substrate heated to 120° C. in an atmosphere of nitrogen and vaporizing mesitylene.

Thus obtained thin film of dimethylpentacene showed a wide angle X-ray diffraction pattern having the diffraction peaks for (00n) planes (n=1, 2, 3, 4 and 5) corresponding to an interplanar distance of 1.68 nm, in which the diffraction peak for the (001) plane showed a half peak width of 0.082 degrees. The interplanar distance was approximately equal to the length of a dimethylpentacene molecule, which is 1.7 nm. Accordingly, it was found that the major axes of the molecules were oriented perpendicular to the surface of a substrate.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 120° C., and spreading the above described dimethylpentacene solution heated to 150° C. on the substrate surface to form a thin film of dimethylpentacene. A transistor was prepared by setting a silicon substrate as a gate electrode, a surface gold electrode as a source/drain electrode and a thin film of dimethylpentacene as a semiconductor layer. Then, field-effect transistor characteristics were evaluated on the transistor. As a result, the transistor showed a mobility of 1.7 $cm^2/V \cdot s$, an on/off current ratio of $1 \times 10^5$, and a threshold voltage of 2.4 V.

EXAMPLE 13

A compound of 2,3-dipropylpentacene-6,13-dihydroxide was obtained by coupling 1,2-dipropylbenzene-4,5-dialdehyde with 1,4-dihydroxyanthracene to synthesize 2,3-dipropylpentacene-6,13-dione, and reducing it. Then, a compound of 2,3-dipropyl-6,13-dichloropentacene (DPDCP) was synthesized by reacting the above obtained compound with N-chlorosuccinimide.

A homogeneous solution was prepared by mixing 30 mg of DPDCP with 10 g of mesitylene in an atmosphere of nitrogen, and then heating the mixture to 150° C. A thin film of DPDCP was formed on a silicon substrate, by spreading the DPDCP solution on the substrate heated to 120° C. in an atmosphere of nitrogen and vaporizing mesitylene.

Thus obtained thin film of DPDCP showed a wide angle X-ray diffraction pattern having the diffraction peaks for (00n) planes (n=1, 2 and 3) corresponding to an interplanar distance of 2.45 nm, in which the diffraction peak for the (001) plane showed a half peak width of 0.174 degrees. The interplanar distance was approximately equal to the length of a DPDCP molecule in a slanting direction (direction of diagonal line), which is 2.3 nm. Accordingly, it was found that the major axes of the molecules were oriented perpendicular to the surface of a substrate.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 120° C., and spreading the above described DPDCP solution heated to 150° C. on the substrate surface to form a thin film of DPDCP. A transistor was prepared by setting a silicon substrate as a gate electrode, a surface gold electrode as a source/drain electrode and a thin film of DPDCP as a semiconductor layer. Then, field-effect transistor characteristics were evaluated on the transistor. As a result, the transistor showed a mobility of 0.3 $cm^2/V \cdot s$, an on/off current ratio of $1 \times 10^4$, and a threshold voltage of 4 V.

EXAMPLE 14

A solution was prepared by mixing 30 mg of rubrene (manufactured by Aldrich Corporation) with 10 g of trichlorobenzene. A thin film of rubrene was formed on a silicon substrate, by spreading the solution heated to 150° C. on the silicon substrate heated to 120° C. and vaporizing trichlorobenzene.

Thus obtained thin film showed a wide angle X-ray diffraction pattern having the diffraction peak corresponding to an interplanar distance of 1.3 nm, in which the diffraction peak showed a half peak width of 0.18 degrees. The interplanar distance was approximately equal to the length of a rubrene molecule, which is 1.35 nm. Accordingly, it was found that the major axes of the molecules were oriented perpendicular to the surface of a substrate.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 120° C., and spreading the above described rubrene solution heated to 150° C. on the substrate surface to form a thin film of rubrene. A transistor was prepared by setting a silicon substrate as a gate electrode, a surface gold electrode as a source/drain electrode and a thin film of rubrene as a semiconductor layer. Then, field-effect transistor characteristics were evaluated on the transistor. As a result, the transistor showed a mobility of $3\times10^{-4}$ cm$^2$/V·s, an on/off current ratio of $1\times10^3$, and a threshold voltage of 5 V.

A transistor prepared with the use of a rubrene thin film formed by vapor deposition did not work (because the current value was 1 nA or less). A wide angle x-ray diffraction pattern of the thin film of rubrene did not show a diffraction peak, which means that the thin film was amorphous.

EXAMPLE 15

A pentacene solution was prepared by mixing 30 mg of pentacene with 10 g of 1,2,4-trichlorobenzene, and then heating the mixture to 200° C. in an atmosphere of nitrogen.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to a predetermined temperature, and spreading the above described pentacene solution heated to 200° C. on the substrate surface to form a pentacene thin film. In addition, the temperatures of the silicon substrate were set at each temperature between 60° C. and 215° C. as shown in Table 1. The temperature of the silicon substrate was measured with the use of an infrared-ray radiation thermometer.

A transistor was prepared by setting a silicon substrate as a gate electrode, a surface gold electrode as a source/drain electrode and a pentacene thin film as a semiconductor layer. Then, field-effect transistor characteristics were evaluated on each of the transistors having the thin film formed at different temperatures of the silicon substrate. The result is shown in Table 1. Here, the electric field-effect mobility was calculated from transfer characteristics measured by scanning a gate voltage from +40 V to −80 V while applying the drain voltage of 60 V.

In addition, a transistor provided with a thin film formed on a silicon substrate of 50° C. worked and showed a mobility of $8\times10^{-3}$ cm$^2$/V·s, an on/off current ratio of 1,000 and a threshold voltage of 11 V, though they are not shown in Table 1.

TABLE 1

| Substrate temperature (° C.) | Electric field-effect mobility (cm$^2$/V · s) | on/off current ratio | Threshold voltage (V) |
| --- | --- | --- | --- |
| 215 | 0.10 | $1 \times 10^4$ | 2.5 |
| 205 | 0.28 | $1 \times 10^5$ | 3.6 |
| 195 | 0.30 | $1 \times 10^5$ | 1.9 |
| 185 | 0.40 | $1 \times 10^5$ | 2.1 |
| 160 | 1.35 | $1 \times 10^5$ | 0.8 |
| 135 | 0.45 | $1 \times 10^5$ | 1.5 |
| 110 | 0.08 | $1 \times 10^5$ | −1.0 |

TABLE 1-continued

| Substrate temperature (° C.) | Electric field-effect mobility (cm$^2$/V · s) | on/off current ratio | Threshold voltage (V) |
| --- | --- | --- | --- |
| 80 | 0.04 | $1 \times 10^5$ | −2.8 |
| 60 | 0.02 | $3 \times 10^4$ | −1.9 |

EXAMPLE 16

A homogeneous solution was prepared by mixing 30 mg of pentacene with 10 g of 1,2,4-trichlorobenzene in an atmosphere of nitrogen, and then heating the mixture to 180° C. Subsequently, the pentacene solution was introduced into a stainless syringe loaded with a spouting needle (with inside diameter of 0.2 mm). Droplets of the pentacene solution were spouted onto a silicon substrate heated to 150° C. while the syringe was kept at 180° C. to form a pattern of a pentacene thin film on the silicon substrate. When the droplets were ejected, a distance between a silicon substrate surface and a spouting part of the ejection needle was controlled to 30 µm. Shot Mini made by Musashi Engineering, Inc. was used as a droplet-spouting device.

Thus obtained pentacene thin film showed a wide angle X-ray diffraction pattern having the diffraction peaks for (00n) planes (n=1, 2, 3, 4, 5 and 6) corresponding to an interplanar distance of 1.45 nm, in which the diffraction peak for the (001) plane showed a half peak width of 0.10 degrees. It was found that the pentacene thin film was the high-crystallinity thin film in which the major axes of the pentacene molecules were oriented perpendicular to the surface of a substrate.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). The electrode pattern consists of channels having W of 500 µm and L of 50 µm formed at every 1 millimeter in a transistor structure. A transistor structure was prepared by heating the silicon substrate having such an electrode pattern formed thereon to 150° C., and spouting droplets of the above described pentacene solution heated to 150° C. to the channel of each transistor on the substrate surface to form a pentacene thin film. In the above step, the spouted pentacene solution spread in a circle so as to cover the channel and was dried to form the pentacene thin film.

A transistor was prepared by setting a silicon substrate as a gate electrode, a surface gold electrode as a source/drain electrode and a pentacene thin film as a semiconductor layer. Then, field-effect transistor characteristics were evaluated on the transistor. As a result, the transistor showed a mobility of 0.10–0.13 cm$^2$/V·s, a non/off current ratio of $1\times10^5$, and a threshold voltage of 0.2 V-0.7 V. Thus, it was found that a thin film pattern of pentacene could be also formed by a printing method.

COMPARATIVE EXAMPLE

A vapor deposition film of pentacene was formed on the silicon substrate of ordinary temperature by a vacuum deposition method. The film was formed in conditions of a growth rate of 0.1 nm/s and a pressure of the atmosphere of $2\times10^{-6}$ Pa.

Figure 10:
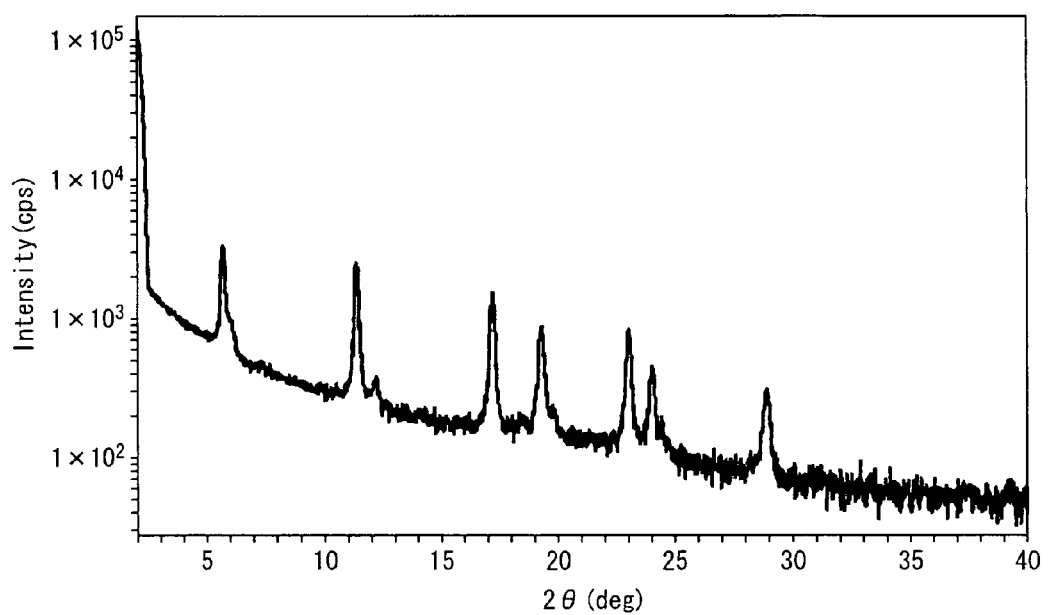
FIG. 10 is a view showing a wide angle X-ray diffraction pattern of a pentacene thin film in Comparative Example.

Thus obtained pentacene thin film showed a wide angle X-ray diffraction pattern (see FIG. 10) having the diffraction peaks for (00n) planes (n=1, 2, 3 and 4) corresponding to two sorts of an interplanar distances (c-axis lattice constant). Specifically, the diffraction pattern showed the diffraction peaks for (00n) planes corresponding to an interplanar distance of 1.45 nm, and the diffraction peaks for (00n) planes corresponding to an interplanar distance of 1.54 nm. Among the above diffraction peaks of (00n) planes, a diffraction peak corresponding to the (001) plane has a half peak width of 0.21 degrees. Thus, it was found that the pentacene thin film in Comparative Example was inferior in crystallinity to that in Example 1.

In addition, a ratio (I)/(I') of the intensity (I) of the diffraction peak for the (001) plane corresponding to the interplanar distance of 1.4 nm or more but less than 1.5 nm (which is the diffraction peak for the (001) plane corresponding to the above described an interplanar distance of 1.45 nm) to the intensity (I') of the diffraction peak for the (001) plane corresponding to the interplanar distance of 1.5 nm or more but less than 1.6 nm (which is the diffraction peak for the (001) plane corresponding to the above described an interplanar distance of 1.54 nm) was 0.5.

As a result of having observed the structure of the obtained pentacene thin film with an AFM, a structure consisting of particulate crystals with an average particle size of 0.1 μm was observed.

As a result of having evaluated field-effect transistor characteristics by the same method as in the case of Example 1, the transistor provided with the vapor-deposited film of pentacene showed a mobility of 0.17 cm$^2$/V·s and a threshold voltage of 25 V.

EXAMPLE 17

A homogeneous solution was prepared by mixing 30 mg of pentacene with 10 g of 1,2,4-trichlorobenzene in an atmosphere of nitrogen, and then heating the mixture to 230° C.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to a predetermined temperature, and spreading the above described pentacene solution heated to 230° C. on the substrate surface to form a pentacene thin film. In addition, the temperatures of the silicon substrate were set at each temperature between 155° C. and 285° C. as shown in Table 2. The temperature of the silicon substrate was measured with the use of an infrared-ray radiation thermometer.

A transistor was prepared by setting a silicon substrate as a gate electrode, a surface gold electrode as a source/drain electrode and a pentacene thin film as a semiconductor layer. Then, field-effect transistor characteristics were evaluated on each of the transistors having the thin film formed at different temperatures of the silicon substrate. The results are shown in Table 2. Here, the electric field-effect mobility was calculated from transfer characteristics measured by scanning a gate voltage from +20 V to −40 V while applying the drain voltage of −45 V.

TABLE 2

| Substrate temperature (° C.) | Electric field-effect mobility (cm$^2$/V · s) | on/off current ratio | Threshold voltage (V) |
| --- | --- | --- | --- |
| 155 | 0.36 | 1 × 10$^5$ | 1.2 |
| 185 | 0.21 | 5 × 10$^5$ | 1.0 |

TABLE 2-continued

| Substrate temperature (° C.) | Electric field-effect mobility (cm$^2$/V · s) | on/off current ratio | Threshold voltage (V) |
| --- | --- | --- | --- |
| 215 | 0.16 | 1 × 10$^5$ | 2.8 |
| 225 | 0.14 | 1 × 10$^4$ | 2.3 |
| 235 | 0.01 | 1 × 10$^3$ | 6.0 |
| 245 | 0.01 | 1 × 10$^3$ | 10 |
| 265 | 0.004 | 1 × 10$^3$ | 5.0 |
| 285 | measurement impossible | measurement impossible | measurement impossible |

EXAMPLE 18

A homogeneous solution was prepared by mixing 5 mg of pentacene with 10 g of o-dichlorobenzene in an atmosphere of nitrogen, and then heating the mixture to 100° C.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to a predetermined temperature, and spreading the above described pentacene solution heated to 100° C. on the substrate surface to form a pentacene thin film. In the above step, the temperature of the silicon substrate was set at 80° C. or 100° C. The temperature of the silicon substrate was measured with the use of an infrared-ray radiation thermometer.

A transistor was prepared by setting a silicon substrate as a gate electrode, a surface gold electrode as a source/drain electrode and a pentacene thin film as a semiconductor layer. Then, field-effect transistor characteristics were evaluated on each of the transistors having the thin film formed at different temperatures of the silicon substrate. Here, the electric field-effect mobility was calculated from transfer characteristics measured by scanning a gate voltage from +20 V to −40 V while applying the drain voltage of −45 V. As a result, the transistor provided with a thin film formed on a silicon substrate of 80° C. showed a mobility of 0.03 cm$^2$/V·s and a threshold voltage of −5 V, and the transistor provided with a thin film formed on a silicon substrate of 100° C. showed a mobility of 0.08 cm$^2$/V·s and a threshold voltage of −2 V. In addition, both transistors showed an on/off current ratio of 1×10$^5$.

EXAMPLE 19

A homogeneous solution was prepared by mixing 30 mg of pentacene with 10 g of 1,2,4-trichlorobenzene in an atmosphere of nitrogen, and then heating the mixture to 245° C. In the above step, the homogeneous solution was prepared by charging the mixture in a cylindrical glass vessel, heating the lower part of the glass vessel on a hot plate, and keeping refluxing 1,2,4-trichlorobenzene which has vaporized and condensed on the wall surface of the glass vessel.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to a predetermined temperature, and spreading the above described pentacene solution heated to 245° C.

on the substrate surface to form a pentacene thin film. In the above step, the temperature of the silicon substrate was set at 230° C. or 235° C. The temperature of the silicon substrate was measured with the use of an infrared-ray radiation thermometer.

A transistor was prepared by setting a silicon substrate as a gate electrode, a surface gold electrode as a source/drain electrode and a pentacene thin film as a semiconductor layer. Then, field-effect transistor characteristics were evaluated on the transistor. Here, the electric field-effect mobility was calculated from transfer characteristics measured by scanning a gate voltage from +20 V to −40 V while applying the drain voltage of −45 V. As a result, the transistor provided with a thin film formed on a silicon substrate of 230° C. showed a mobility of 0.03 cm$^2$/V·s, an on/off current ratio of 8×10$^3$, and a threshold voltage of −12 V. On the other hand, some transistors provided with a thin film formed on a silicon substrate of 235° C. worked and showed a mobility of 0.001 cm$^2$/V·s, and an on/off current ratio of about 1×10$^3$, but most of the transistors did not work.

COMPARATIVE EXAMPLE 2

A mixture prepared by mixing 5 mg of pentacene and 10 g of 1,2,4-trichlorobenzene was heated to 50° C. for two hours. However, pentacene was not dissolved in the solvent and remained in the mixture, and in other words, a homogeneous solution was not formed. Then, a solution was prepared which has a low concentration of pentacene, namely, contains a reduced amount of pentacene. Specifically, a homogeneous solution was prepared by mixing 1 mg of pentacene with 10 g of 1,2,4-trichlorobenzene, and then heating the mixture to 50° C.

Subsequently, as in the case of Example 1, a pattern of a gold electrode was formed as a source/drain electrode on the surface of a silicon substrate heavily doped with an n-type dopant (provided with an oxide layer with the thickness of 200 nm on its surface). A transistor structure was prepared by heating the silicon substrate having such an electrode pattern formed thereon to 50° C., and spreading the above described pentacene solution heated to 50° C. on the substrate surface to form a pentacene thin film. However, the pentacene solution had low concentration and 1,2,4-trichlorobenzene slowly vaporized, so that one hour was necessary to form the thin film required.

A transistor was prepared by setting a silicon substrate as a gate electrode, a surface gold electrode as a source/drain electrode and a pentacene thin film as a semiconductor layer. Then, field-effect transistor characteristics were evaluated on the transistor. Here, the electric field-effect mobility was calculated from transfer characteristics measured by scanning a gate voltage from +20 V to −40 V while applying the drain voltage of −45 V. As a result, some transistors worked and showed a mobility of 0.005 cm$^2$/V·s and an on/off current ratio of about 1×10$^3$, but most of the transistors did not work.

INDUSTRIAL APPLICABILITY

The present invention is preferably applicable to the fields of electronics, photonics and bioelectronics.

The invention claimed is:

1. A method for preparing a condensed polycyclic aromatic compound thin film, the method comprising:
dissolving at a temperature of 60° C. to 250° C. a condensed polycyclic aromatic compound in a solvent containing an organic compound having a higher vapor pressure than that of the condensed polycyclic aromatic compound to form a solution;
spreading the solution having a temperature of 60° C. to 250° C. over a base having a temperature of 60° C. to 230° C.; and
removing the organic compound and the solvent from the solution spread over the base while maintaining a supersaturating state to form a condensed polycyclic aromatic compound thin film having the condensed polycyclic aromatic compound,
wherein the content of the organic compound in the solution is 30 mass % to 99.9 mass %.

2. The method for preparing a condensed polycyclic aromatic compound thin film according to claim 1, characterized in that the condensed polycyclic aromatic compound is at least one of a polyacene compound and a derivative thereof.

3. The method for preparing a condensed polycyclic aromatic compound thin film according to claim 1, characterized in that the condensed polycyclic aromatic compound is at least one of pentacene, a derivative of pentacene, hexacene and a derivative of hexacene.

4. The method for preparing a condensed polycyclic aromatic compound thin film according to claim 1, characterized in that the temperature of the solution when the condensed polycyclic aromatic compound is dissolved in the solvent and the temperature of the solution when it is spread over the base are higher than 70° C. but 240° C. or lower.

5. The method for preparing a condensed polycyclic aromatic compound thin film according to claim 1, characterized in that the temperature of the solution when the condensed polycyclic aromatic compound is dissolved in the solvent and the temperature of the solution when it is spread over the base are higher than 80° C. but 230° C. or lower.

6. The method for preparing a condensed polycyclic aromatic compound thin film according to claim 1, characterized in that the temperature of the solution when the condensed polycyclic aromatic compound is dissolved in the solvent and the temperature of the solution when it is spread over the base are higher than 100° C. but 220° C. or lower.

7. The method for preparing a condensed polycyclic aromatic compound thin film according to claim 1, characterized in that the temperature of the base is higher than 70° C. but 220° C. or lower.

8. The method for preparing a condensed polycyclic aromatic compound thin film according to claim 1, characterized in that the temperature of the base is higher than 80° C. but 210° C. or lower.

9. The method for preparing a condensed polycyclic aromatic compound thin film according to claim 1, characterized in that the temperature of the solution when spread over the base is equal to or higher than the temperature of the base.

10. The method for preparing a condensed polycyclic aromatic compound thin film according to claim 1, characterized in that a value obtained by subtracting the temperature of the base from the temperature of the solution is −15° C. to 190° C.

11. The method for preparing a condensed polycyclic aromatic compound thin film according to claim 1, characterized in that a value obtained by subtracting the temperature of the base from the temperature of the solution is 0° C. to 100° C.

12. The method for preparing a condensed polycyclic aromatic compound thin film according to claim 1, characterized in that a value obtained by subtracting the temperature of the base from the temperature of the solution is 0° C. to 80° C.

13. The method for preparing a condensed polycyclic aromatic compound thin film according to claim 1, characterized in that the method is conducted in an inert gas atmosphere.

14. The method for preparing a condensed polycyclic aromatic compound thin film according to claim 1, using a condensed polycyclic aromatic compound purified by reducing the amount of impurities, the method comprising:
dissolving at a temperature of 60° C. to 250° C. a condensed polycyclic aromatic compound in a solvent containing an organic compound having a higher vapor pressure than that of the condensed polycyclic aromatic compound at a temperature of 60° C. to 250° C. to form a solution; and
cooling the solution or mixing the solution with either ethanol or acetone to precipitate a crystal of the condensed polycyclic aromatic compound from the solution.

15. A condensed polycyclic aromatic compound thin film characterized in that the condensed polycyclic aromatic compound thin film is obtained by the method for preparing a condensed polycyclic aromatic compound thin film according to claim 1.

16. The condensed polycyclic. aromatic compound thin film according to claim 15, characterized in that the thin film is a condensed polycyclic aromatic compound thin film having crystallinity, and a molecule of a condensed polycyclic aromatic compound is oriented so that the major axis of the molecule is perpendicular to the surface of the thin film, and shows a wide angle x-ray diffraction pattern having a half peak width of a diffraction peak for a (001) plane among the diffraction peaks for (00n) planes of 0.05 deg to 0.2 deg.

17. The condensed polycyclic aromatic compound thin film according to claim 16, characterized in that the thin film has at least one of a structure consisting of plate crystals with particle sizes of 3 μm or larger and a structure having plate crystals extended into a sheet shape.

18. An organic semiconductor device characterized in that at least a part of the organic semiconductor device is constituted by the condensed polycyclic aromatic compound thin film according to claim 15.

19. A pentacene thin film obtained by the method for producing a condensed polycyclic aromatic compound thin film according to claim 1, characterized in that the film shows a wide angle X-ray diffraction pattern having diffraction peaks for (00n) planes (n is an integer of 1 or more) corresponding to an interplanar distance of 1.4 nm or more but less than 1.5 nm, in which a ratio (I)/(I') of the intensity (I) of a diffraction peak for a (001) plane among the diffraction peaks to the intensity (I') of a diffraction peak for a (001) plane corresponding to an interplanar distance of 1.5 nm or more but less than 1.6 nm exceeds 10, and a half peak width of the diffraction peak for a (001) plane among the diffraction peaks for (00n) planes (n is an integer of 1 or more) corresponding to an interplanar distance of 1.4 nm or more but less than 1.5 nm is 0.08 deg to 0.2 deg.

20. An organic semiconductor device characterized in that at least a part of the organic semiconductor device is constituted by the pentacene thin film according to claim 19.

* * * * *